(12) United States Patent
Wen et al.

(10) Patent No.: US 10,815,286 B2
(45) Date of Patent: Oct. 27, 2020

(54) FUSION PROTEIN FOR TREATING INTESTINAL DISEASES

(71) Applicant: ZHEJIANG DOER BIOLOGICS CORPORATION, Hangzhou, Zhejiang (CN)

(72) Inventors: Xiaofang Wen, Zhejiang (CN); Yanshan Huang, Zhejiang (CN); Zhiyu Yang, Zhejiang (CN); Gaofeng Yao, Zhejiang (CN); Yonglu Chen, Zhejiang (CN); Xuelian Wang, Zhejiang (CN)

(73) Assignee: ZHEJIANG DOER BIOLOGICS CORPORATION, Hangzhou, Zhejiang (CN)

( * ) Notice: Subject to any disclaimer, the term of this patent is extended or adjusted under 35 U.S.C. 154(b) by 0 days.

(21) Appl. No.: 16/302,642

(22) PCT Filed: Oct. 18, 2017

(86) PCT No.: PCT/CN2017/106727
§ 371 (c)(1),
(2) Date: Nov. 18, 2018

(87) PCT Pub. No.: WO2018/077098
PCT Pub. Date: May 3, 2018

(65) Prior Publication Data
US 2019/0241639 A1  Aug. 8, 2019

(30) Foreign Application Priority Data
Oct. 27, 2016  (CN) .......................... 2016 1 0957019

(51) Int. Cl.
*C07K 14/605* (2006.01)
*A61P 1/00* (2006.01)
*C07K 14/72* (2006.01)
*A61K 38/26* (2006.01)
*A61K 47/64* (2017.01)
*C12N 15/62* (2006.01)
*C07K 19/00* (2006.01)
*A61K 38/00* (2006.01)
*A61P 39/00* (2006.01)

(52) U.S. Cl.
CPC ............ *C07K 14/605* (2013.01); *A61K 38/26* (2013.01); *A61K 47/64* (2017.08); *A61P 1/00* (2018.01); *A61P 39/00* (2018.01); *C07K 14/723* (2013.01); *C07K 19/00* (2013.01); *C12N 15/62* (2013.01); *A61K 38/00* (2013.01); *C07K 2319/30* (2013.01); *C07K 2319/31* (2013.01)

(58) Field of Classification Search
None
See application file for complete search history.

(56) References Cited

FOREIGN PATENT DOCUMENTS

| CN | 101171262 A | | 4/2008 | |
|---|---|---|---|---|
| WO | WO 2007/067828 | * | 6/2007 | ............... C12N 5/06 |
| WO | WO 2007067828 A2 | | 6/2007 | |

* cited by examiner

*Primary Examiner* — Elly-Gerald Stoica
(74) *Attorney, Agent, or Firm* — Global IP Services; Tianhua Gu

(57) ABSTRACT

The invention provides fusion proteins for treating an intestinal disease, having a structure as follows: R-L-P, wherein R is a GLP-2 receptor agonist; L is a peptide linker; and P is a long-acting carrier protein. The fusion protein provided by the invention has significant bioactivities and in vitro stability.

7 Claims, 2 Drawing Sheets
Specification includes a Sequence Listing.

SEQUENCE LISTING

```
<160> NUMBER OF SEQ ID NOS: 101

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 33
<212> TYPE: PRT
<213> ORGANISM: Homo sapiens

<400> SEQUENCE: 2

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 3
<211> LENGTH: 30
<212> TYPE: PRT
<213> ORGANISM: Homo sapiens

<400> SEQUENCE: 3

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys
            20                  25                  30
```

```
<210> SEQ ID NO 4
<211> LENGTH: 27
<212> TYPE: PRT
<213> ORGANISM: Homo sapiens

<400> SEQUENCE: 4

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile
            20                  25

<210> SEQ ID NO 5
<211> LENGTH: 227
<212> TYPE: PRT
<213> ORGANISM: Homo sapiens

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 6
<211> LENGTH: 229
<212> TYPE: PRT
<213> ORGANISM: Homo sapiens

<400> SEQUENCE: 6

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30
```

Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 7
<211> LENGTH: 226
<212> TYPE: PRT
<213> ORGANISM: Homo sapiens

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro 165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 8
<211> LENGTH: 228
<212> TYPE: PRT
<213> ORGANISM: Homo sapiens

<400> SEQUENCE: 8

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Ala Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 9
<211> LENGTH: 261
<212> TYPE: PRT
<213> ORGANISM: Homo sapiens

<400> SEQUENCE: 9

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr

```
                    20                  25                  30
Asp Glu Ser Lys Tyr Gly Pro Pro Cys Pro Pro Cys Pro Ala Pro Glu
                35                  40                  45

Phe Leu Gly Gly Pro Ser Val Phe Leu Phe Pro Pro Lys Pro Lys Asp
         50                  55                  60

Thr Leu Met Ile Ser Arg Thr Pro Glu Val Thr Cys Val Val Val Asp
 65                  70                  75                  80

Val Ser Gln Glu Asp Pro Glu Val Gln Phe Asn Trp Tyr Val Asp Gly
                 85                  90                  95

Val Glu Val His Asn Ala Lys Thr Lys Pro Arg Glu Glu Gln Phe Ala
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Gly Leu Pro
    130                 135                 140

Ser Ser Ile Glu Lys Thr Ile Ser Lys Ala Lys Gly Gln Pro Arg Glu
145                 150                 155                 160

Pro Gln Val Tyr Thr Leu Pro Pro Ser Gln Glu Met Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Arg
    210                 215                 220

Leu Thr Val Asp Lys Ser Arg Trp Gln Glu Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Leu Gly
            260

<210> SEQ ID NO 10
<211> LENGTH: 266
<212> TYPE: PRT
<213> ORGANISM: Homo sapiens

<400> SEQUENCE: 10

His Gly Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
                20                  25                  30

Asp Gly Gly Gly Ser Glu Ser Lys Tyr Gly Pro Pro Cys Pro Pro
            35                  40                  45

Cys Pro Ala Pro Glu Phe Leu Gly Gly Pro Ser Val Phe Leu Phe Pro
        50                  55                  60

Pro Lys Pro Lys Asp Thr Leu Met Ile Ser Arg Thr Pro Glu Val Thr
 65                  70                  75                  80

Cys Val Val Val Asp Val Ser Gln Glu Asp Pro Glu Val Gln Phe Asn
                 85                  90                  95

Trp Tyr Val Asp Gly Val Glu Val His Asn Ala Lys Thr Lys Pro Arg
            100                 105                 110

Glu Glu Gln Phe Ala Ser Thr Tyr Arg Val Val Ser Val Leu Thr Val
        115                 120                 125
```

```
Leu His Gln Asp Trp Leu Asn Gly Lys Glu Tyr Lys Cys Lys Val Ser
    130                 135                 140
Asn Lys Gly Leu Pro Ser Ser Ile Glu Lys Thr Ile Ser Lys Ala Lys
145                 150                 155                 160
Gly Gln Pro Arg Glu Pro Gln Val Tyr Thr Leu Pro Pro Ser Gln Glu
                165                 170                 175
Glu Met Thr Lys Asn Gln Val Ser Leu Thr Cys Leu Val Lys Gly Phe
            180                 185                 190
Tyr Pro Ser Asp Ile Ala Val Glu Trp Glu Ser Asn Gly Gln Pro Glu
        195                 200                 205
Asn Asn Tyr Lys Thr Thr Pro Pro Val Leu Asp Ser Asp Gly Ser Phe
210                 215                 220
Phe Leu Tyr Ser Arg Leu Thr Val Asp Lys Ser Arg Trp Gln Glu Gly
225                 230                 235                 240
Asn Val Phe Ser Cys Ser Val Met His Glu Ala Leu His Asn His Tyr
                245                 250                 255
Thr Gln Lys Ser Leu Ser Leu Ser Leu Gly
            260                 265

<210> SEQ ID NO 11
<211> LENGTH: 276
<212> TYPE: PRT
<213> ORGANISM: Homo sapiens

<400> SEQUENCE: 11

His Gly Asp Gly Ser Phe Ser Asp Glu Met Asn Thr Ile Leu Asp Asn
1               5                   10                  15
Leu Ala Ala Arg Asp Phe Ile Asn Trp Leu Ile Gln Thr Lys Ile Thr
                20                  25                  30
Asp Gly Gly Gly Ser Gly Gly Gly Ser Gly Gly Gly Ser
            35                  40                  45
Glu Ser Lys Tyr Gly Pro Pro Cys Pro Pro Cys Pro Ala Pro Glu Phe
    50                  55                  60
Leu Gly Gly Pro Ser Val Phe Leu Phe Pro Pro Lys Pro Lys Asp Thr
65                  70                  75                  80
Leu Met Ile Ser Arg Thr Pro Glu Val Thr Cys Val Val Val Asp Val
                85                  90                  95
Ser Gln Glu Asp Pro Glu Val Gln Phe Asn Trp Tyr Val Asp Gly Val
            100                 105                 110
Glu Val His Asn Ala Lys Thr Lys Pro Arg Glu Glu Gln Phe Ala Ser
        115                 120                 125
Thr Tyr Arg Val Val Ser Val Leu Thr Val Leu His Gln Asp Trp Leu
130                 135                 140
Asn Gly Lys Glu Tyr Lys Cys Lys Val Ser Asn Lys Gly Leu Pro Ser
145                 150                 155                 160
Ser Ile Glu Lys Thr Ile Ser Lys Ala Lys Gly Gln Pro Arg Glu Pro
                165                 170                 175
Gln Val Tyr Thr Leu Pro Pro Ser Gln Glu Glu Met Thr Lys Asn Gln
            180                 185                 190
Val Ser Leu Thr Cys Leu Val Lys Gly Phe Tyr Pro Ser Asp Ile Ala
        195                 200                 205
Val Glu Trp Glu Ser Asn Gly Gln Pro Glu Asn Asn Tyr Lys Thr Thr
    210                 215                 220
Pro Pro Val Leu Asp Ser Asp Gly Ser Phe Phe Leu Tyr Ser Arg Leu
225                 230                 235                 240
```

```
Thr Val Asp Lys Ser Arg Trp Gln Glu Gly Asn Val Phe Cys Ser
            245                 250                 255

Val Met His Glu Ala Leu His Asn His Tyr Thr Gln Lys Ser Leu Ser
        260                 265                 270

Leu Ser Leu Gly
        275

<210> SEQ ID NO 12
<211> LENGTH: 269
<212> TYPE: PRT
<213> ORGANISM: Homo sapiens

<400> SEQUENCE: 12

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Ser Gly Pro Ala Glu Ser Lys Tyr Gly Pro Pro
        35                  40                  45

Cys Pro Pro Cys Pro Ala Pro Glu Phe Leu Gly Gly Pro Ser Val Phe
    50                  55                  60

Leu Phe Pro Pro Lys Pro Lys Asp Thr Leu Met Ile Ser Arg Thr Pro
65                  70                  75                  80

Glu Val Thr Cys Val Val Asp Val Ser Gln Glu Asp Pro Glu Val
                85                  90                  95

Gln Phe Asn Trp Tyr Val Asp Gly Val Glu Val His Asn Ala Lys Thr
            100                 105                 110

Lys Pro Arg Glu Glu Gln Phe Ala Ser Thr Tyr Arg Val Val Ser Val
        115                 120                 125

Leu Thr Val Leu His Gln Asp Trp Leu Asn Gly Lys Glu Tyr Lys Cys
130                 135                 140

Lys Val Ser Asn Lys Gly Leu Pro Ser Ser Ile Glu Lys Thr Ile Ser
145                 150                 155                 160

Lys Ala Lys Gly Gln Pro Arg Glu Pro Gln Val Tyr Thr Leu Pro Pro
                165                 170                 175

Ser Gln Glu Glu Met Thr Lys Asn Gln Val Ser Leu Thr Cys Leu Val
            180                 185                 190

Lys Gly Phe Tyr Pro Ser Asp Ile Ala Val Glu Trp Glu Ser Asn Gly
        195                 200                 205

Gln Pro Glu Asn Asn Tyr Lys Thr Thr Pro Pro Val Leu Asp Ser Asp
    210                 215                 220

Gly Ser Phe Phe Leu Tyr Ser Arg Leu Thr Val Asp Lys Ser Arg Trp
225                 230                 235                 240

Gln Glu Gly Asn Val Phe Ser Cys Ser Val Met His Glu Ala Leu His
                245                 250                 255

Asn His Tyr Thr Gln Lys Ser Leu Ser Leu Ser Leu Gly
            260                 265

<210> SEQ ID NO 13
<211> LENGTH: 272
<212> TYPE: PRT
<213> ORGANISM: Homo sapiens

<400> SEQUENCE: 13

His Gly Asp Gly Ser Phe Ser Asp Glu Met Asn Thr Ile Leu Asp Asn
1               5                   10                  15
```

```
Leu Ala Ala Arg Asp Phe Ile Asn Trp Leu Ile Gln Thr Lys Ile Thr
            20                  25                  30

Asp Gly Gly Gly Ser Gly Gly Gly Ser Gly Pro Gln Asp Lys
        35                  40                  45

Thr His Thr Cys Pro Pro Cys Pro Ala Pro Glu Leu Leu Gly Gly Pro
 50                  55                  60

Ser Val Phe Leu Phe Pro Pro Lys Pro Lys Asp Thr Leu Met Ile Ser
65                   70                  75                  80

Arg Thr Pro Glu Val Thr Cys Val Val Val Asp Val Ser His Glu Asp
                85                  90                  95

Pro Glu Val Lys Phe Asn Trp Tyr Val Asp Gly Val Glu Val His Asn
            100                 105                 110

Ala Lys Thr Lys Pro Arg Glu Glu Gln Tyr Ala Ser Thr Tyr Arg Val
        115                 120                 125

Val Ser Val Leu Thr Val Leu His Gln Asp Trp Leu Asn Gly Lys Glu
130                 135                 140

Tyr Lys Cys Lys Val Ser Asn Lys Ala Leu Pro Ala Pro Ile Glu Lys
145                 150                 155                 160

Thr Ile Ser Lys Ala Lys Gly Gln Pro Arg Glu Pro Gln Val Tyr Thr
                165                 170                 175

Leu Pro Pro Ser Arg Asp Glu Leu Thr Lys Asn Gln Val Ser Leu Thr
            180                 185                 190

Cys Leu Val Lys Gly Phe Tyr Pro Ser Asp Ile Ala Val Glu Trp Glu
        195                 200                 205

Ser Asn Gly Gln Pro Glu Asn Asn Tyr Lys Thr Thr Pro Pro Val Leu
210                 215                 220

Asp Ser Asp Gly Ser Phe Phe Leu Tyr Ser Lys Leu Thr Val Asp Lys
225                 230                 235                 240

Ser Arg Trp Gln Gln Gly Asn Val Phe Ser Cys Ser Val Met His Glu
                245                 250                 255

Ala Leu His Asn His Tyr Thr Gln Lys Ser Leu Ser Leu Ser Pro Gly
            260                 265                 270

<210> SEQ ID NO 14
<211> LENGTH: 279
<212> TYPE: PRT
<213> ORGANISM: Homo sapiens

<400> SEQUENCE: 14

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Ser Gly Gly Gly Ser Gly Gly Gly Ser
        35                  40                  45

Gly Pro Ala Glu Ser Lys Tyr Gly Pro Pro Cys Pro Pro Cys Pro Ala
50                  55                  60

Pro Glu Phe Leu Gly Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Asp Val Ser Gln Glu Asp Pro Glu Val Gln Phe Asn Trp Tyr Val
            100                 105                 110

Asp Gly Val Glu Val His Asn Ala Lys Thr Lys Pro Arg Glu Glu Gln
```

```
                    115                 120                 125
Phe Ala Ser Thr Tyr Arg Val Ser Val Leu Thr Val Leu His Gln
                130                 135                 140
Asp Trp Leu Asn Gly Lys Glu Tyr Lys Cys Lys Val Ser Asn Lys Gly
145                 150                 155                 160
Leu Pro Ser Ser Ile Glu Lys Thr Ile Ser Lys Ala Lys Gly Gln Pro
                    165                 170                 175
Arg Glu Pro Gln Val Tyr Thr Leu Pro Pro Ser Gln Glu Glu Met Thr
                180                 185                 190
Lys Asn Gln Val Ser Leu Thr Cys Leu Val Lys Gly Phe Tyr Pro Ser
                    195                 200                 205
Asp Ile Ala Val Glu Trp Glu Ser Asn Gly Gln Pro Glu Asn Asn Tyr
                210                 215                 220
Lys Thr Thr Pro Pro Val Leu Asp Ser Asp Gly Ser Phe Phe Leu Tyr
225                 230                 235                 240
Ser Arg Leu Thr Val Asp Lys Ser Arg Trp Gln Glu Gly Asn Val Phe
                    245                 250                 255
Ser Cys Ser Val Met His Glu Ala Leu His Asn His Tyr Thr Gln Lys
                260                 265                 270
Ser Leu Ser Leu Ser Leu Gly
                275

<210> SEQ ID NO 15
<211> LENGTH: 289
<212> TYPE: PRT
<213> ORGANISM: Homo sapiens

<400> SEQUENCE: 15

His Gly Asp Gly Ser Phe Ser Asp Glu Met Asn Thr Ile Leu Asp Asn
1               5                   10                  15
Leu Ala Ala Arg Asp Phe Ile Asn Trp Leu Ile Gln Thr Lys Ile Thr
                20                  25                  30
Asp Gly Gly Gly Gly Ser Gly Gly Gly Gly Ser Gly Gly Gly Gly Ser
                35                  40                  45
Gly Gly Gly Gly Ser Gly Gly Gly Ser Gly Pro Asp Glu Ser Lys
50                  55                  60
Tyr Gly Pro Pro Cys Pro Pro Cys Pro Ala Pro Glu Phe Leu Gly Gly
65                  70                  75                  80
Pro Ser Val Phe Leu Phe Pro Pro Lys Pro Lys Asp Thr Leu Met Ile
                85                  90                  95
Ser Arg Thr Pro Glu Val Thr Cys Val Val Val Asp Val Ser Gln Glu
                100                 105                 110
Asp Pro Glu Val Gln Phe Asn Trp Tyr Val Asp Gly Val Glu Val His
                115                 120                 125
Asn Ala Lys Thr Lys Pro Arg Glu Glu Gln Phe Ala Ser Thr Tyr Arg
                130                 135                 140
Val Val Ser Val Leu Thr Val Leu His Gln Asp Trp Leu Asn Gly Lys
145                 150                 155                 160
Glu Tyr Lys Cys Lys Val Ser Asn Lys Gly Leu Pro Ser Ser Ile Glu
                    165                 170                 175
Lys Thr Ile Ser Lys Ala Lys Gly Gln Pro Arg Glu Pro Gln Val Tyr
                180                 185                 190
Thr Leu Pro Pro Ser Gln Glu Glu Met Thr Lys Asn Gln Val Ser Leu
                195                 200                 205
```

```
Thr Cys Leu Val Lys Gly Phe Tyr Pro Ser Asp Ile Ala Val Glu Trp
    210                 215                 220
Glu Ser Asn Gly Gln Pro Glu Asn Asn Tyr Lys Thr Thr Pro Pro Val
225                 230                 235                 240
Leu Asp Ser Asp Gly Ser Phe Phe Leu Tyr Ser Arg Leu Thr Val Asp
                245                 250                 255
Lys Ser Arg Trp Gln Glu Gly Asn Val Phe Ser Cys Ser Val Met His
                260                 265                 270
Glu Ala Leu His Asn His Tyr Thr Gln Lys Ser Leu Ser Leu Ser Leu
                275                 280                 285
Gly

<210> SEQ ID NO 16
<211> LENGTH: 277
<212> TYPE: PRT
<213> ORGANISM: Homo sapiens

<400> SEQUENCE: 16

His Gly Asp Gly Ser Phe Ser Asp Glu Met Asn Thr Ile Leu Asp Asn
1               5                   10                  15
Leu Ala Ala Arg Asp Phe Ile Asn Trp Leu Ile Gln Thr Lys Ile Thr
                20                  25                  30
Asp Gly Gly Gly Ser Gly Gly Gly Ser Gly Pro Pro Gly Pro
                35                  40                  45
Ala Glu Ser Lys Tyr Gly Pro Pro Cys Pro Pro Cys Pro Ala Pro Glu
    50                  55                  60
Phe Leu Gly Gly Pro Ser Val Phe Leu Phe Pro Pro Lys Pro Lys Asp
65                  70                  75                  80
Thr Leu Met Ile Ser Arg Thr Pro Glu Val Thr Cys Val Val Val Asp
                85                  90                  95
Val Ser Gln Glu Asp Pro Glu Val Gln Phe Asn Trp Tyr Val Asp Gly
    100                 105                 110
Val Glu Val His Asn Ala Lys Thr Lys Pro Arg Glu Glu Gln Phe Ala
    115                 120                 125
Ser Thr Tyr Arg Val Val Ser Val Leu Thr Val Leu His Gln Asp Trp
    130                 135                 140
Leu Asn Gly Lys Glu Tyr Lys Cys Lys Val Ser Asn Lys Gly Leu Pro
145                 150                 155                 160
Ser Ser Ile Glu Lys Thr Ile Ser Lys Ala Lys Gly Gln Pro Arg Glu
                165                 170                 175
Pro Gln Val Tyr Thr Leu Pro Pro Ser Gln Glu Glu Met Thr Lys Asn
                180                 185                 190
Gln Val Ser Leu Thr Cys Leu Val Lys Gly Phe Tyr Pro Ser Asp Ile
                195                 200                 205
Ala Val Glu Trp Glu Ser Asn Gly Gln Pro Glu Asn Asn Tyr Lys Thr
    210                 215                 220
Thr Pro Pro Val Leu Asp Ser Asp Gly Ser Phe Phe Leu Tyr Ser Arg
225                 230                 235                 240
Leu Thr Val Asp Lys Ser Arg Trp Gln Glu Gly Asn Val Phe Ser Cys
                245                 250                 255
Ser Val Met His Glu Ala Leu His Asn His Tyr Thr Gln Lys Ser Leu
                260                 265                 270
Ser Leu Ser Leu Gly
                275
```

```
<210> SEQ ID NO 17
<211> LENGTH: 275
<212> TYPE: PRT
<213> ORGANISM: Homo sapiens

<400> SEQUENCE: 17

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Ser Gly Gly Gly Ser Gly Pro Pro Gly Pro
        35                  40                  45

Ala Asp Lys Thr His Thr Cys Pro Pro Cys Pro Ala Pro Glu Leu Leu
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

His Glu Asp Pro Glu Val Lys Phe Asn Trp Tyr Val Asp Gly Val Glu
            100                 105                 110

Val His Asn Ala Lys Thr Lys Pro Arg Glu Glu Gln Tyr Ala Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Ala Leu Pro Ala Pro
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Arg Asp Glu Leu Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Lys Leu Thr
225                 230                 235                 240

Val Asp Lys Ser Arg Trp Gln Gln Gly Asn Val Phe Ser Cys Ser Val
                245                 250                 255

Met His Glu Ala Leu His Asn His Tyr Thr Gln Lys Ser Leu Ser Leu
            260                 265                 270

Ser Pro Gly
        275

<210> SEQ ID NO 18
<211> LENGTH: 280
<212> TYPE: PRT
<213> ORGANISM: Homo sapiens

<400> SEQUENCE: 18

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Ser Gly Gly Gly Ser Gly Pro Glu Gly Ala
        35                  40                  45
```

```
Pro Gly Pro Ser Glu Ser Lys Tyr Gly Pro Pro Cys Pro
    50              55                  60

Ala Pro Glu Phe Leu Gly Gly Pro Ser Val Phe Leu Phe Pro Pro Lys
65              70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
            115                 120                 125

Gln Phe Ala Ser Thr Tyr Arg Val Val Ser Val Leu Thr Val Leu His
130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
            195                 200                 205

Ser Asp Ile Ala Val Glu Trp Glu Ser Asn Gly Gln Pro Glu Asn Asn
210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly
275                 280

<210> SEQ ID NO 19
<211> LENGTH: 286
<212> TYPE: PRT
<213> ORGANISM: Homo sapiens

<400> SEQUENCE: 19

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20                  25                  30

Asp Gly Gly Gly Ser Gly Gly Gly Ser Gly Pro Ser Gly Ala
            35                  40                  45

Pro Gly Pro Pro Gly Pro Glu Gly Pro Ala Glu Ser Lys Tyr Gly Pro
    50                  55                  60

Pro Cys Pro Pro Cys Pro Ala Pro Glu Phe Leu Gly Gly Pro Ser Val
65              70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser Gln Glu Asp Pro Glu
            100                 105                 110

Val Gln Phe Asn Trp Tyr Val Asp Gly Val Glu Val His Asn Ala Lys
            115                 120                 125

Thr Lys Pro Arg Glu Glu Gln Phe Ala Ser Thr Tyr Arg Val Val Ser
130                 135                 140
```

```
Val Leu Thr Val Leu His Gln Asp Trp Leu Asn Gly Lys Glu Tyr Lys
145                 150                 155                 160

Cys Lys Val Ser Asn Lys Gly Leu Pro Ser Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Gln Glu Glu Met Thr Lys Asn Gln Val Ser Leu Thr Cys Leu
            195                 200                 205

Val Lys Gly Phe Tyr Pro Ser Asp Ile Ala Val Glu Trp Glu Ser Asn
210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Arg Leu Thr Val Asp Lys Ser Arg
                245                 250                 255

Trp Gln Glu Gly Asn Val Phe Ser Cys Ser Val Met His Glu Ala Leu
            260                 265                 270

His Asn His Tyr Thr Gln Lys Ser Leu Ser Leu Ser Leu Gly
            275                 280                 285

<210> SEQ ID NO 20
<211> LENGTH: 298
<212> TYPE: PRT
<213> ORGANISM: Homo sapiens

<400> SEQUENCE: 20

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Ser Gly Gly Gly Gly Ser Gly Pro Ser Gly Ala
            35                  40                  45

Pro Gly Pro Pro Gly Pro Ser Gly Ala Pro Gly Pro Pro Gly Pro Ser
    50                  55                  60

Gly Ala Pro Gly Pro Pro Glu Ser Lys Tyr Gly Pro Pro Cys Pro Pro
65                  70                  75                  80

Cys Pro Ala Pro Glu Phe Leu Gly Gly Pro Ser Val Phe Leu Phe Pro
                85                  90                  95

Pro Lys Pro Lys Asp Thr Leu Met Ile Ser Arg Thr Pro Glu Val Thr
            100                 105                 110

Cys Val Val Val Asp Val Ser Gln Glu Asp Pro Glu Val Gln Phe Asn
            115                 120                 125

Trp Tyr Val Asp Gly Val Glu Val His Asn Ala Lys Thr Lys Pro Arg
130                 135                 140

Glu Glu Gln Phe Ala Ser Thr Tyr Arg Val Val Ser Val Leu Thr Val
145                 150                 155                 160

Leu His Gln Asp Trp Leu Asn Gly Lys Glu Tyr Lys Cys Lys Val Ser
                165                 170                 175

Asn Lys Gly Leu Pro Ser Ser Ile Glu Lys Thr Ile Ser Lys Ala Lys
            180                 185                 190

Gly Gln Pro Arg Glu Pro Gln Val Tyr Thr Leu Pro Pro Ser Gln Glu
            195                 200                 205

Glu Met Thr Lys Asn Gln Val Ser Leu Thr Cys Leu Val Lys Gly Phe
210                 215                 220

Tyr Pro Ser Asp Ile Ala Val Glu Trp Glu Ser Asn Gly Gln Pro Glu
```

```
                225                 230                 235                 240
Asn Asn Tyr Lys Thr Thr Pro Pro Val Leu Asp Ser Asp Gly Ser Phe
                245                 250                 255

Phe Leu Tyr Ser Arg Leu Thr Val Asp Lys Ser Arg Trp Gln Glu Gly
                260                 265                 270

Asn Val Phe Ser Cys Ser Val Met His Glu Ala Leu His Asn His Tyr
                275                 280                 285

Thr Gln Lys Ser Leu Ser Leu Ser Leu Gly
                290                 295

<210> SEQ ID NO 21
<211> LENGTH: 316
<212> TYPE: PRT
<213> ORGANISM: Homo sapiens

<400> SEQUENCE: 21

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20                  25                  30

Asp Gly Gly Gly Ser Gly Gly Gly Ser Gly Pro Ala Gly Glu
            35                  40                  45

Pro Gly Pro Ser Gly Pro Ala Gly Glu Pro Gly Pro Ser Gly Pro Ala
        50                  55                  60

Gly Glu Pro Gly Pro Ser Gly Pro Ala Gly Glu Pro Gly Pro Ser Gly
65                  70                  75                  80

Pro Ala Gly Glu Pro Gly Pro Ser Glu Ser Lys Tyr Gly Pro Pro Cys
                85                  90                  95

Pro Pro Cys Pro Ala Pro Glu Phe Leu Gly Gly Pro Ser Val Phe Leu
            100                 105                 110

Phe Pro Pro Lys Pro Lys Asp Thr Leu Met Ile Ser Arg Thr Pro Glu
        115                 120                 125

Val Thr Cys Val Val Val Asp Val Ser Gln Glu Asp Pro Glu Val Gln
    130                 135                 140

Phe Asn Trp Tyr Val Asp Gly Val Glu Val His Asn Ala Lys Thr Lys
145                 150                 155                 160

Pro Arg Glu Glu Gln Phe Ala Ser Thr Tyr Arg Val Val Ser Val Leu
                165                 170                 175

Thr Val Leu His Gln Asp Trp Leu Asn Gly Lys Glu Tyr Lys Cys Lys
            180                 185                 190

Val Ser Asn Lys Gly Leu Pro Ser Ser Ile Glu Lys Thr Ile Ser Lys
        195                 200                 205

Ala Lys Gly Gln Pro Arg Glu Pro Gln Val Tyr Thr Leu Pro Pro Ser
    210                 215                 220

Gln Glu Glu Met Thr Lys Asn Gln Val Ser Leu Thr Cys Leu Val Lys
225                 230                 235                 240

Gly Phe Tyr Pro Ser Asp Ile Ala Val Glu Trp Glu Ser Asn Gly Gln
                245                 250                 255

Pro Glu Asn Asn Tyr Lys Thr Thr Pro Pro Val Leu Asp Ser Asp Gly
            260                 265                 270

Ser Phe Phe Leu Tyr Ser Arg Leu Thr Val Asp Lys Ser Arg Trp Gln
        275                 280                 285

Glu Gly Asn Val Phe Ser Cys Ser Val Met His Glu Ala Leu His Asn
    290                 295                 300
```

```
His Tyr Thr Gln Lys Ser Leu Ser Leu Ser Leu Gly
305                 310                 315
```

```
<210> SEQ ID NO 22
<211> LENGTH: 331
<212> TYPE: PRT
<213> ORGANISM: Homo sapiens

<400> SEQUENCE: 22
```

```
His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20                  25                  30

Asp Gly Gly Gly Ser Gly Gly Gly Ser Gly Pro Pro Gly Pro
            35                  40                  45

Ala Gly Pro Pro Gly Pro Ala Gly Pro Gly Pro Ala Gly Pro Pro
50                  55                          60

Gly Pro Ala Gly Pro Gly Pro Ala Gly Pro Gly Pro Ala Gly
65                  70                  75                  80

Pro Pro Gly Pro Ala Gly Pro Gly Pro Ala Gly Pro Gly Pro
                85                  90                  95

Ala Gly Pro Pro Gly Pro Ala Glu Ser Lys Tyr Gly Pro Pro Cys Pro
                100                 105                 110

Pro Cys Pro Ala Pro Glu Phe Leu Gly Gly Pro Ser Val Phe Leu Phe
            115                 120                 125

Pro Pro Lys Pro Lys Asp Thr Leu Met Ile Ser Arg Thr Pro Glu Val
130                 135                 140

Thr Cys Val Val Val Asp Val Ser Gln Glu Asp Pro Glu Val Gln Phe
145                 150                 155                 160

Asn Trp Tyr Val Asp Gly Val Glu Val His Asn Ala Lys Thr Lys Pro
                165                 170                 175

Arg Glu Glu Gln Phe Ala Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Gly Leu Pro Ser Ser Ile Glu Lys Thr Ile Ser Lys Ala
210                 215                 220

Lys Gly Gln Pro Arg Glu Pro Gln Val Tyr Thr Leu Pro Pro Ser Gln
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Arg Leu Thr Val Asp Lys Ser Arg Trp Gln Glu
290                 295                 300

Gly Asn Val Phe Ser Cys Ser Val Met His Glu Ala Leu His Asn His
305                 310                 315                 320

Tyr Thr Gln Lys Ser Leu Ser Leu Ser Leu Gly
                325                 330
```

```
<210> SEQ ID NO 23
<211> LENGTH: 270
<212> TYPE: PRT
<213> ORGANISM: Homo sapiens
```

<400> SEQUENCE: 23

```
His Gly Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Asp Pro Ser Ser Gly Ala Pro Pro Ser Glu Ser Lys Tyr Gly Pro
        35                  40                  45

Pro Cys Pro Pro Cys Pro Ala Pro Glu Phe Leu Gly Gly Pro Ser Val
    50                  55                  60

Phe Leu Phe Pro Pro Lys Pro Lys Asp Thr Leu Met Ile Ser Arg Thr
65                  70                  75                  80

Pro Glu Val Thr Cys Val Val Val Asp Val Ser Gln Glu Asp Pro Glu
                85                  90                  95

Val Gln Phe Asn Trp Tyr Val Asp Gly Val Glu Val His Asn Ala Lys
            100                 105                 110

Thr Lys Pro Arg Glu Glu Gln Phe Ala Ser Thr Tyr Arg Val Val Ser
        115                 120                 125

Val Leu Thr Val Leu His Gln Asp Trp Leu Asn Gly Lys Glu Tyr Lys
    130                 135                 140

Cys Lys Val Ser Asn Lys Gly Leu Pro Ser Ser Ile Glu Lys Thr Ile
145                 150                 155                 160

Ser Lys Ala Lys Gly Gln Pro Arg Glu Pro Gln Val Tyr Thr Leu Pro
                165                 170                 175

Pro Ser Gln Glu Glu Met Thr Lys Asn Gln Val Ser Leu Thr Cys Leu
            180                 185                 190

Val Lys Gly Phe Tyr Pro Ser Asp Ile Ala Val Glu Trp Glu Ser Asn
        195                 200                 205

Gly Gln Pro Glu Asn Asn Tyr Lys Thr Thr Pro Pro Val Leu Asp Ser
    210                 215                 220

Asp Gly Ser Phe Phe Leu Tyr Ser Arg Leu Thr Val Asp Lys Ser Arg
225                 230                 235                 240

Trp Gln Glu Gly Asn Val Phe Ser Cys Ser Val Met His Glu Ala Leu
                245                 250                 255

His Asn His Tyr Thr Gln Lys Ser Leu Ser Leu Ser Leu Gly
            260                 265                 270
```

<210> SEQ ID NO 24
<211> LENGTH: 260
<212> TYPE: PRT
<213> ORGANISM: Homo sapiens

<400> SEQUENCE: 24

```
His Gly Asp Gly Ser Phe Ser Asp Glu Met Asn Thr Ile Leu Asp Asn
 1               5                  10                  15

Leu Ala Ala Arg Asp Phe Ile Asn Trp Leu Ile Gly Gly Gly Gly Ser
            20                  25                  30

Glu Ser Lys Tyr Gly Pro Pro Cys Pro Pro Cys Pro Ala Pro Glu Phe
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser Gln Glu Asp Pro Glu Val Gln Phe Asn Trp Tyr Val Asp Gly Val
                85                  90                  95
```

Glu Val His Asn Ala Lys Thr Lys Pro Arg Glu Gln Phe Ala Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Gly Leu Pro Ser
    130                 135                 140

Ser Ile Glu Lys Thr Ile Ser Lys Ala Lys Gly Gln Pro Arg Glu Pro
145                 150                 155                 160

Gln Val Tyr Thr Leu Pro Pro Ser Gln Glu Glu Met Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Arg Leu
    210                 215                 220

Thr Val Asp Lys Ser Arg Trp Gln Glu Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Leu Gly
            260

<210> SEQ ID NO 25
<211> LENGTH: 268
<212> TYPE: PRT
<213> ORGANISM: Homo sapiens

<400> SEQUENCE: 25

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Gly Gly
            20                  25                  30

Gly Gly Ser Gly Gly Gly Gly Ser Glu Ser Lys Tyr Gly Pro Pro Cys
        35                  40                  45

Pro Pro Cys Pro Ala Pro Glu Phe Leu Gly Gly Pro Ser Val Phe Leu
    50                  55                  60

Phe Pro Pro Lys Pro Lys Asp Thr Leu Met Ile Ser Arg Thr Pro Glu
65                  70                  75                  80

Val Thr Cys Val Val Val Asp Val Ser Gln Glu Asp Pro Glu Val Gln
                85                  90                  95

Phe Asn Trp Tyr Val Asp Gly Val Glu Val His Asn Ala Lys Thr Lys
            100                 105                 110

Pro Arg Glu Glu Gln Phe Ala Ser Thr Tyr Arg Val Val Ser Val Leu
        115                 120                 125

Thr Val Leu His Gln Asp Trp Leu Asn Gly Lys Glu Tyr Lys Cys Lys
    130                 135                 140

Val Ser Asn Lys Gly Leu Pro Ser Ser Ile Glu Lys Thr Ile Ser Lys
145                 150                 155                 160

Ala Lys Gly Gln Pro Arg Glu Pro Gln Val Tyr Thr Leu Pro Pro Ser
                165                 170                 175

Gln Glu Glu Met Thr Lys Asn Gln Val Ser Leu Thr Cys Leu Val Lys
            180                 185                 190

Gly Phe Tyr Pro Ser Asp Ile Ala Val Glu Trp Glu Ser Asn Gly Gln

```
                    195                 200                 205
Pro Glu Asn Asn Tyr Lys Thr Thr Pro Pro Val Leu Asp Ser Asp Gly
210                 215                 220

Ser Phe Phe Leu Tyr Ser Arg Leu Thr Val Asp Lys Ser Arg Trp Gln
225                 230                 235                 240

Glu Gly Asn Val Phe Ser Cys Ser Val Met His Glu Ala Leu His Asn
                245                 250                 255

His Tyr Thr Gln Lys Ser Leu Ser Leu Ser Leu Gly
            260                 265

<210> SEQ ID NO 26
<211> LENGTH: 269
<212> TYPE: PRT
<213> ORGANISM: Homo sapiens

<400> SEQUENCE: 26

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Pro Ser Ser Gly Ala
                20                  25                  30

Pro Pro Pro Ser Gly Gly Gly Ser Glu Ser Lys Tyr Gly Pro Pro
            35                  40                  45

Cys Pro Pro Cys Pro Ala Pro Glu Phe Leu Gly Gly Pro Ser Val Phe
50                  55                  60

Leu Phe Pro Pro Lys Pro Lys Asp Thr Leu Met Ile Ser Arg Thr Pro
65                  70                  75                  80

Glu Val Thr Cys Val Val Val Asp Val Ser Gln Glu Asp Pro Glu Val
                85                  90                  95

Gln Phe Asn Trp Tyr Val Asp Gly Val Glu Val His Asn Ala Lys Thr
            100                 105                 110

Lys Pro Arg Glu Glu Gln Phe Ala Ser Thr Tyr Arg Val Val Ser Val
        115                 120                 125

Leu Thr Val Leu His Gln Asp Trp Leu Asn Gly Lys Glu Tyr Lys Cys
130                 135                 140

Lys Val Ser Asn Lys Gly Leu Pro Ser Ser Ile Glu Lys Thr Ile Ser
145                 150                 155                 160

Lys Ala Lys Gly Gln Pro Arg Glu Pro Gln Val Tyr Thr Leu Pro Pro
                165                 170                 175

Ser Gln Glu Glu Met Thr Lys Asn Gln Val Ser Leu Thr Cys Leu Val
            180                 185                 190

Lys Gly Phe Tyr Pro Ser Asp Ile Ala Val Glu Trp Glu Ser Asn Gly
        195                 200                 205

Gln Pro Glu Asn Asn Tyr Lys Thr Thr Pro Pro Val Leu Asp Ser Asp
210                 215                 220

Gly Ser Phe Phe Leu Tyr Ser Arg Leu Thr Val Asp Lys Ser Arg Trp
225                 230                 235                 240

Gln Glu Gly Asn Val Phe Ser Cys Ser Val Met His Glu Ala Leu His
                245                 250                 255

Asn His Tyr Thr Gln Lys Ser Leu Ser Leu Ser Leu Gly
            260                 265

<210> SEQ ID NO 27
<211> LENGTH: 280
<212> TYPE: PRT
<213> ORGANISM: Homo sapiens
```

<400> SEQUENCE: 27

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Asn Gly
            20                  25                  30

Gly Pro Ser Ser Gly Ala Pro Pro Ser Gly Gly Gly Ser Gly
        35                  40                  45

Gly Gly Gly Ser Glu Ser Lys Tyr Gly Pro Pro Cys Pro Pro Cys Pro
    50                  55                  60

Ala Pro Glu Phe Leu Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
        115                 120                 125

Gln Phe Ala Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Arg Leu Thr Val Asp Lys Ser Arg Trp Gln Glu Gly Asn Val
                245                 250                 255

Phe Ser Cys Ser Val Met His Glu Ala Leu His Asn His Tyr Thr Gln
            260                 265                 270

Lys Ser Leu Ser Leu Ser Leu Gly
        275                 280

<210> SEQ ID NO 28
<211> LENGTH: 278
<212> TYPE: PRT
<213> ORGANISM: Homo sapiens

<400> SEQUENCE: 28

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Asn Gly Gly Pro Ser
            20                  25                  30

Ser Gly Ala Pro Pro Ser Gly Gly Gly Ser Gly Pro Ala Gly
        35                  40                  45

Pro Asn Glu Ser Lys Tyr Gly Pro Pro Cys Pro Pro Cys Pro Ala Pro
    50                  55                  60

Glu Phe Leu Gly Gly Pro Ser Val Phe Leu Phe Pro Pro Lys Pro Lys
65                  70                  75                  80

-continued

Asp Thr Leu Met Ile Ser Arg Thr Pro Glu Val Thr Cys Val Val Val
                85                  90                  95

Asp Val Ser Gln Glu Asp Pro Glu Val Gln Phe Asn Trp Tyr Val Asp
            100                 105                 110

Gly Val Glu Val His Asn Ala Lys Thr Lys Pro Arg Glu Glu Gln Phe
        115                 120                 125

Ala Ser Thr Tyr Arg Val Val Ser Val Leu Thr Val Leu His Gln Asp
    130                 135                 140

Trp Leu Asn Gly Lys Glu Tyr Lys Cys Lys Val Ser Asn Lys Gly Leu
145                 150                 155                 160

Pro Ser Ser Ile Glu Lys Thr Ile Ser Lys Ala Lys Gly Gln Pro Arg
                165                 170                 175

Glu Pro Gln Val Tyr Thr Leu Pro Pro Ser Gln Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Asn Gly Gln Pro Glu Asn Asn Tyr Lys
    210                 215                 220

Thr Thr Pro Pro Val Leu Asp Ser Asp Gly Ser Phe Phe Leu Tyr Ser
225                 230                 235                 240

Arg Leu Thr Val Asp Lys Ser Arg Trp Gln Glu Gly Asn Val Phe Ser
                245                 250                 255

Cys Ser Val Met His Glu Ala Leu His Asn His Tyr Thr Gln Lys Ser
            260                 265                 270

Leu Ser Leu Ser Leu Gly
        275

<210> SEQ ID NO 29
<211> LENGTH: 275
<212> TYPE: PRT
<213> ORGANISM: Homo sapiens

<400> SEQUENCE: 29

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Pro Ser
                20                  25                  30

Ser Gly Ala Pro Pro Pro Ser Gly Gly Gly Ser Gly Pro Ala Glu
            35                  40                  45

Ser Lys Tyr Gly Pro Pro Cys Pro Pro Cys Pro Ala Pro Glu Phe Leu
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Ala Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

```
Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
    275

<210> SEQ ID NO 30
<211> LENGTH: 16
<212> TYPE: PRT
<213> ORGANISM: Homo sapiens

<400> SEQUENCE: 30

Gly Gly Gly Gly Ser Gly Gly Gly Ser Gly Pro Pro Gly Pro Ala
1               5                   10                  15

<210> SEQ ID NO 31
<211> LENGTH: 19
<212> TYPE: PRT
<213> ORGANISM: Homo sapiens

<400> SEQUENCE: 31

Gly Gly Gly Gly Ser Gly Gly Gly Ser Gly Pro Glu Gly Ala Pro
1               5                   10                  15

Gly Pro Ser

<210> SEQ ID NO 32
<211> LENGTH: 25
<212> TYPE: PRT
<213> ORGANISM: Homo sapiens

<400> SEQUENCE: 32

Gly Gly Gly Gly Ser Gly Gly Gly Ser Gly Pro Ser Gly Ala Pro
1               5                   10                  15

Gly Pro Pro Gly Pro Glu Gly Pro Ala
            20                  25

<210> SEQ ID NO 33
<211> LENGTH: 814
<212> TYPE: DNA
<213> ORGANISM: Homo sapiens

<400> SEQUENCE: 33
gtactcgaga aaagacatgg tgatggttct ttctctgatg agatgaacac cattcttgat      60
aaccttgccg ccagagactt tatcaactgg ttgattcaga ccaagatcac tgacgagtcc     120
aaatatggtc ccccatgccc accttgccca gcacctgagt tcctgggagg accatcagtc     180
tttctgttcc ccccaaaacc caaggatact tgatgatttt ccagaactcc tgaagttact     240
tgtgttgtgg ttgatgtctc tcaagaggac ccagaagttc aatttaactg gtacgttgat     300
ggtgttgaag ttcataacgc taagactaag ccaagagaag aacaatttgc ttctacttac     360
```

```
agagttgttt ctgttttgac tgttttgcat caagattggt tgaacggtaa ggaatacaag    420
tgtaaggtct ccaacaaagg ccttccgtcc tccatcgaga aaaccatctc caaggctaag    480
ggtcaaccaa gagaaccaca agtttacact ttgccaccat ctcaagaaga aatgactaag    540
aaccaagttt ctttgacttg tttggttaag ggttttacc catctgacat tgctgttgaa     600
tgggaatcta acggtcaacc agaaaacaac tataagacta ctccaccagt tttggattct    660
gatggttctt tcttcttgta ctccagattg actgttgaca agtcaagatg gcaggaggga    720
aatgtcttct catgctccgt gatgcatgag gctctgcaca accactacac acagaagagt    780
ctttccctgt ctttaggtta ataggaattc cggt                                814
```

<210> SEQ ID NO 34
<211> LENGTH: 829
<212> TYPE: DNA
<213> ORGANISM: Homo sapiens

<400> SEQUENCE: 34

```
gtactcgaga aaagacatgg tgatggttct ttctctgatg agatgaacac cattcttgat    60
aaccttgccg ccagagactt tatcaactgg ttgattcaga ccaagatcac tgacggtggt    120
ggtggttctg agtccaaata tggtccccca tgcccaccct gcccagcacc tgagttcctg    180
ggaggaccat cagtctttct gttccccca aaacccaagg atactttgat gatttccaga    240
actcctgaag ttacttgtgt tgtggttgat gtctctcaag aggacccaga agttcaattt    300
aactggtacg ttgatggtgt tgaagttcat aacgctaaga ctaagccaag agaagaacaa    360
tttgcttcta cttacagagt tgtttctgtt ttgactgttt tgcatcaaga ttggttgaac    420
ggtaaggaat acaagtgtaa ggtctccaac aaaggccttc cgtcctccat cgagaaaacc    480
atctccaagg ctagggtca accaagagaa ccacaagttt acactttgcc accatctcaa    540
gaagaaatga ctaagaacca agtttctttg acttgtttgg ttaagggttt ttacccatct    600
gacattgctg ttgaatggga atctaacggt caaccagaaa acaactataa gactactcca    660
ccagttttgg attctgatgg ttctttcttc ttgtactcca gattgactgt tgacaagtca    720
agatggcagg agggaaatgt cttctcatgc tccgtgatgc atgaggctct gcacaaccac    780
tacacacaga gagtctttc cctgtcttta ggttaatagg aattccggt                 829
```

<210> SEQ ID NO 35
<211> LENGTH: 859
<212> TYPE: DNA
<213> ORGANISM: Homo sapiens

<400> SEQUENCE: 35

```
gtactcgaga aaagacatgg tgatggttct ttctctgatg agatgaacac cattcttgat    60
aaccttgccg ccagagactt tatcaactgg ttgattcaga ccaagatcac tgacggtggt    120
ggtggttctg aggaggagg atctggcgg ggcggcagtg agtccaaata tggtccccca    180
tgcccacctt gcccagcacc tgagttcctg ggaggaccat cagtctttct gttccccca    240 aaacccaagg atactttgat gatttccaga actcctgaag ttacttgtgt tgtggttgat    300
gtctctcaag aggacccaga agttcaattt aactggtacg ttgatggtgt tgaagttcat    360
aacgctaaga ctaagccaag agaagaacaa tttgcttcta cttacagagt tgtttctgtt    420
ttgactgttt tgcatcaaga ttggttgaac ggtaaggaat acaagtgtaa ggtctccaac    480
aaaggccttc cgtcctccat cgagaaaacc atctccaagg ctaagggtca accaagagaa    540
```

```
ccacaagttt acactttgcc accatctcaa gaagaaatga ctaagaacca agtttctttg    600
acttgtttgg ttaagggttt ttacccatct gacattgctg ttgaatggga atctaacggt    660
caaccagaaa acaactataa gactactcca ccagttttgg attctgatgg ttctttcttc    720
ttgtactcca gattgactgt tgacaagtca agatggcagg agggaaatgt cttctcatgc    780
tccgtgatgc atgaggctct gcacaaccac tacacacaga gagtctttc cctgtcttta    840 ggttaatagg aattccggt                                                 859

<210> SEQ ID NO 36
<211> LENGTH: 838
<212> TYPE: DNA
<213> ORGANISM: Homo sapiens

<400> SEQUENCE: 36
gtactcgaga aaagacatgg tgatggttct ttctctgatg agatgaacac cattcttgat     60
aaccttgccg ccagagactt tatcaactgg ttgattcaga ccaagatcac tgacggtggt    120
ggtggttctg gacctgctga gtccaaatat ggtcccccat gcccaccttg cccagcacct    180
gagttcctgg gaggaccatc agtctttctg ttcccccccaa aacccaagga tactttgatg    240
atttccagaa ctcctgaagt tacttgtgtt gtggttgatg tctctcaaga ggacccagaa    300
gttcaattta ctggtacgt tgatggtgtt gaagttcata cgctaagac taagccaaga    360 gaagaacaat ttgcttctac ttacagagtt gtttctgttt tgactgtttt gcatcaagat    420
tggttgaacg gtaaggaata caagtgtaag gtctccaaca aaggccttcc gtcctccatc    480
gagaaaacca tctccaaggc taagggtcaa ccaagagaac acaagtttac actttgcca    540 ccatctcaag aagaaatgac taagaaccaa gtttctttga cttgtttggt taagggtttt    600
tacccatctg acattgctgt tgaatgggaa tctaacggtc aaccagaaaa caactataag    660
actactccac cagttttgga ttctgatggt tctttcttct tgtactccag attgactgtt    720
gacaagtcaa gatggcagga gggaaatgtc ttctcatgct ccgtgatgca tgaggctctg    780
cacaaccact acacacagaa gagtctttcc ctgtctttag gttaatagga attccggt     838

<210> SEQ ID NO 37
<211> LENGTH: 846
<212> TYPE: DNA
<213> ORGANISM: Homo sapiens

<400> SEQUENCE: 37
gtactcgaga aaagacatgg tgatggttct ttctctgatg agatgaacac cattcttgat     60
aaccttgccg ccagagactt tatcaactgg ttgattcaga ccaagatcac tgacggtggt    120
ggtggttctg gaggaggagg atctggacct caagacaaaa ctcacacatg cccaccgtgc    180
ccagcacctg aactcctggg tggaccgtca gtcttcctct tccccccaaa acccaaggat    240
actttgatga tttccagaac tccagaagtt acttgtgttg ttgttgatgt ttctcatgaa    300
gatccagaag ttaagtttaa ctggtacgtt gatggtgttg aagttcataa cgctaagact    360
aagccaagag aagaacaata cgcttctact tacagagttg tttctgtttt gactgttttg    420
catcaagatt ggttgaatgg aaaggagtac aagtgcaagg tctccaacaa agccctccca    480
gcccccatcg agaaaaccat ctccaaagct aagggtcaac caagagaacc acaagtttac    540
actttgccac catcaagaga tgaattgact aagaaccaag tttctttgac ttgtttggtt    600
aagggttttt acccatctga tattgctgtt gaatgggaat ctaacggtca accagagaac    660
aactacaaga ccacgcctcc cgtgctggac tccgacggat cttcttct gtactctaag    720
```

```
ttgactgttg ataagagtag atggcaacaa ggtaacgttt ttagttgttc tgttatgcat    780
gaagctctgc acaaccacta cacgcagaag tctctctccc tgtctccggg ttaataggaa    840
ttctag                                                               846
```

<210> SEQ ID NO 38
<211> LENGTH: 868
<212> TYPE: DNA
<213> ORGANISM: Homo sapiens

<400> SEQUENCE: 38

```
gtactcgaga aaagacatgg tgatggttct ttctctgatg agatgaacac cattcttgat     60
aaccttgccg ccagagactt tatcaactgg ttgattcaga ccaagatcac tgacggtggt    120
ggtggttctg gaggaggagg atctggcggc ggcggcagtg gacctgctga gtccaaatat    180
ggtcccccat gcccaccttg cccagcacct gagttcctgg gaggaccatc agtctttctg    240
ttccccccaa aacccaagga tactttgatg atttccagaa ctcctgaagt tacttgtgtt    300
gtggttgatg tctctcaaga ggacccagaa gttcaattta ctggtacgt tgatggtgtt     360 gaagttcata cgctaagac taagccaaga gaagaacaat ttgcttctac ttacagagtt    420
gtttctgttt tgactgtttt gcatcaagat tggttgaacg gtaaggaata caagtgtaag    480
gtctccaaca aaggccttcc gtcctccatc gagaaaacca tctccaaggc taagggtcaa    540
ccaagagaac acaagtttta cactttgcca ccatctcaag aagaaatgac taagaaccaa    600
gtttctttga cttgtttggt taagggtttt tacccatctg acattgctgt tgaatgggaa    660
tctaacggtc aaccagaaaa caactataag actactccac cagttttgga ttctgatggt    720 tcttctcttct tgtactccag attgactgtt gacaagtcaa gatggcagga gggaaatgtc    780
ttctcatgct ccgtgatgca tgaggctctg cacaaccact acacacagaa gagtctttcc    840
ctgtctttag gttaatagga attccggt                                       868
```

<210> SEQ ID NO 39
<211> LENGTH: 898
<212> TYPE: DNA
<213> ORGANISM: Homo sapiens

<400> SEQUENCE: 39

```
gtactcgaga aaagacatgg tgatggttct ttctctgatg agatgaacac cattcttgat     60
aaccttgccg ccagagactt tatcaactgg ttgattcaga ccaagatcac tgacggtggt    120
ggtggttctg gaggaggagg atctggcggc ggcggcagtg gtggaggcgg gtctggcgga    180
ggtggtagtg gacctgatga gtccaaatat ggtcccccat gcccaccttg cccagcacct    240
gagttcctgg gaggaccatc agtctttctg ttccccccaa aacccaagga tactttgatg    300
atttccagaa ctcctgaagt tacttgtgtt gtggttgatg tctctcaaga ggacccagaa    360
gttcaattta ctggtacgt tgatggtgtt gaagttcata cgctaagac taagccaaga     420 gaagaacaat ttgcttctac ttacagagtt gtttctgttt tgactgtttt gcatcaagat    480
tggttgaacg gtaaggaata caagtgtaag gtctccaaca aaggccttcc gtcctccatc    540
gagaaaacca tctccaaggc taagggtcaa ccaagagaac acaagtttta cactttgcca    600
ccatctcaag aagaaatgac taagaaccaa gtttctttga cttgtttggt taagggtttt    660
tacccatctg acattgctgt tgaatgggaa tctaacggtc aaccagaaaa caactataag    720
actactccac cagttttgga ttctgatggt tcttctcttct tgtactccag attgactgtt    780
```

```
gacaagtcaa gatggcagga gggaaatgtc ttctcatgct ccgtgatgca tgaggctctg    840
cacaaccact acacacagaa gagtctttcc ctgtctttag gttaatagga attccggt     898

<210> SEQ ID NO 40
<211> LENGTH: 862
<212> TYPE: DNA
<213> ORGANISM: Homo sapiens

<400> SEQUENCE: 40
gtactcgaga aaagacatgg tgatggttct ttctctgatg agatgaacac cattcttgat     60
aaccttgccg ccagagactt tatcaactgg ttgattcaga ccaagatcac tgacggtggt    120
ggtggttctg gaggaggagg atctggccca ccaggacctg ctgagtccaa atatggtccc    180
ccatgcccac cttgcccagc acctgagttc ctgggaggac catcagtctt tctgttcccc    240
ccaaaaccca aggatacttt gatgatttcc agaactcctg aagttacttg tgttgtggtt    300
gatgtctctc aagaggaccc agaagttcaa tttaactggt acgttgatgg tgttgaagtt    360
cataacgcta agactaagcc aagagaagaa caatttgctt ctacttacag agttgtttct    420
gttttgactg ttttgcatca agattggttg aacggtaagg aatacaagtg taaggtctcc    480
aacaaaggcc ttccgtcctc catcgagaaa accatctcca aggctaaggg tcaaccaaga    540
gaaccacaag tttacacttt gccaccatct caagaagaaa tgactaagaa ccaagtttct    600
ttgacttgtt tggttaaggg ttttgccca tctgacattg ctgttgaatg gaatctaac     660 ggtcaaccag aaaacaacta taagactact ccaccagttt tggattctga tggttctttc    720
ttcttgtact ccagattgac tgttgacaag tcaagatggc aggagggaaa tgtcttctca    780
tgctccgtga tgcatgaggc tctgcacaac cactacacac agaagagtct ttccctgtct    840
ttaggttaat aggaattccg gt                                            862

<210> SEQ ID NO 41
<211> LENGTH: 855
<212> TYPE: DNA
<213> ORGANISM: Homo sapiens

<400> SEQUENCE: 41
gtactcgaga aaagacatgg tgatggttct ttctctgatg agatgaacac cattcttgat     60
aaccttgccg ccagagactt tatcaactgg ttgattcaga ccaagatcac tgacggtggt    120
ggtggttctg gaggaggagg atctggccca ccaggacctg ctgacaaaac tcacacatgc    180
ccaccgtgcc cagcacctga actcctgggt ggaccgtcag tcttcctctt ccccccaaaa    240
cccaaggata ctttgatgat ttccagaact ccagaagtta cttgtgttgt tgttgatgtt    300
tctcatgaag atccagaagt taagtttaac tggtacgttg atggtgttga agttcataac    360
gctaagacta agccaagaga agaacaatac gcttctactt acagagttgt ttctgttttg    420
actgttttgc atcaagattg gttgaatgga aggagtaca agtgcaaggt ctccaacaaa    480
gccctcccag ccccatcga gaaaaccatc tccaaagcta agggtcaacc aagagaacca    540
caagtttaca ctttgccacc atcaagagat gaattgacta agaaccaagt ttctttgact    600
tgtttggtta agggttttta cccatctgat attgctgttg aatgggaatc taacggtcaa    660
ccagagaaca actacaagac cacgcctccc gtgctggact ccgacggatc tttcttcttg    720
tactctaagt tgactgttga taagagtaga tggcaacaag gtaacgtttt tagttgttct    780
gttatgcatg aagctctgca caaccactac acgcagaagt ctctctcccct gtctccgggt    840 taataggaat tctag                                                    855
```

<210> SEQ ID NO 42
<211> LENGTH: 871
<212> TYPE: DNA
<213> ORGANISM: Homo sapiens

<400> SEQUENCE: 42

| | | | | |
|---|---|---|---|---|
| gtactcgaga | aaagacatgg | tgatggttct | ttctctgatg | agatgaacac | cattcttgat | 60 |
| aaccttgccg | ccagagactt | tatcaactgg | ttgattcaga | ccaagatcac | tgacggtggt | 120 |
| ggtggttctg | gaggaggagg | atctggtcca | gaaggtgctc | caggtccatc | tgagtccaaa | 180 |
| tatggtcccc | catgcccacc | ttgcccagca | cctgagttcc | tgggaggacc | atcagtcttt | 240 |
| ctgttccccc | caaaacccaa | ggatactttg | atgatttcca | gaactcctga | agttacttgt | 300 |
| gttgtggttg | atgtctctca | agaggaccca | gaagttcaat | ttaactggta | cgttgatggt | 360 |
| gttgaagttc | ataacgctaa | gactaagcca | agagaagaac | aatttgcttc | tacttacaga | 420 |
| gttgtttctg | ttttgactgt | tttgcatcaa | gattggttga | acggtaagga | atacaagtgt | 480 |
| aaggtctcca | acaaaggcct | tccgtcctcc | atcgagaaaa | ccatctccaa | ggctaagggt | 540 |
| caaccaagag | aaccacaagt | ttacactttg | ccaccatctc | aagaagaaat | gactaagaac | 600 |
| caagtttctt | tgacttgttt | ggttaagggt | ttttacccat | ctgacattgc | tgttgaatgg | 660 |
| gaatctaacg | gtcaaccaga | aaacaactat | aagactactc | caccagtttt | ggattctgat | 720 |
| ggttcttttct | tcttgtactc | cagattgact | gttgacaagt | caagatggca | ggagggaaat | 780 |
| gtcttctcat | gctccgtgat | gcatgaggct | ctgcacaacc | actacacaca | gaagagtctt | 840 |
| tccctgtctt | taggttaata | ggaattccgg | t | | | 871 |

<210> SEQ ID NO 43
<211> LENGTH: 889
<212> TYPE: DNA
<213> ORGANISM: Homo sapiens

<400> SEQUENCE: 43

| | | | | |
|---|---|---|---|---|
| gtactcgaga | aaagacatgg | tgatggttct | ttctctgatg | agatgaacac | cattcttgat | 60 |
| aaccttgccg | ccagagactt | tatcaactgg | ttgattcaga | ccaagatcac | tgacggtggt | 120 |
| ggtggttctg | gaggaggagg | atctggtcca | tctggtgctc | caggtccacc | aggtccagaa | 180 |
| ggtccagctg | agtccaaata | tggtcccccca | tgcccacctt | gcccagcacc | tgagttcctg | 240 |
| ggaggaccat | cagtcttttct | gttccccccca | aaacccaagg | atactttgat | gatttccaga | 300 |
| actcctgaag | ttacttgtgt | tgtggttgat | gtctctcaag | gacccaga | agttcaattt | 360 |
| aactggtacg | ttgatggtgt | tgaagttcat | aacgctaaga | ctaagccaag | agaagaacaa | 420 |
| tttgcttcta | cttacagagt | tgtttctgtt | ttgactgttt | tgcatcaaga | ttggttgaac | 480 |
| ggtaaggaat | acaagtgtaa | ggtctccaac | aaaggccttc | cgtcctccat | cgagaaaacc | 540 |
| atctccaagg | ctaagggtca | accaagagaa | ccacaagttt | acactttgcc | accatctcaa | 600 |
| gaagaaatga | ctaagaacca | agtttctttg | acttgtttgg | ttaagggttt | ttacccatct | 660 |
| gacattgctg | ttgaatggga | atctaacggt | caaccagaaa | acaactataa | gactactcca | 720 |
| ccagttttgg | attctgatgg | ttctttcttc | ttgtactcca | gattgactgt | tgacaagtca | 780 |
| agatggcagg | agggaaatgt | cttctcatgc | tccgtgatgc | atgaggctct | gcacaaccac | 840 |
| tacacacaga | agagtctttc | cctgtcttta | ggttaatagg | aattccggt | | 889 |

<210> SEQ ID NO 44

<211> LENGTH: 925
<212> TYPE: DNA
<213> ORGANISM: Homo sapiens

<400> SEQUENCE: 44

```
gtactcgaga aaagacatgg tgatggttct ttctctgatg agatgaacac cattcttgat        60
aaccttgccg ccagagactt tatcaactgg ttgattcaga ccaagatcac tgacggtggt       120
ggtggttctg gaggaggagg atctggtcca tctggtgctc caggtccacc aggaccttcc       180
ggagcccctg gtcctcctgg tccttccgga gcccccggcc cgcctgagtc caaatatggt       240
cccccatgcc caccttgccc agcacctgag ttcctgggag gaccatcagt ctttctgttc       300
cccccaaaac ccaaggatac tttgatgatt ccagaactc ctgaagttac ttgtgttgtg        360
gttgatgtct ctcaagagga cccagaagtt caatttaact ggtacgttga tggtgttgaa       420
gttcataacg ctaagactaa gccaagagaa gaacaatttg cttctactta cagagttgtt       480
tctgttttga ctgttttgca tcaagattgg ttgaacggta aggaatacaa gtgtaaggtc       540
tccaacaaag gccttccgtc ctccatcgag aaaaccatct ccaaggctaa gggtcaacca       600
agagaaccac aagtttacac tttgccacca ctctcaagaa gaatgactaa gaaccaagtt       660
tctttgactt gtttggttaa gggtttttac ccatctgaca ttgctgttga atgggaatct       720
aacggtcaac cagaaaacaa ctataagact actccaccag ttttggattc tgatggttct       780
ttcttcttgt actccagatt gactgttgac aagtcaagat ggcaggaggg aaatgtcttc       840
tcatgctccg tgatgcatga ggctctgcac aaccactaca cacagaagag tctttccctg       900
tctttaggtt aataggaatt ccggt                                             925
```

<210> SEQ ID NO 45
<211> LENGTH: 979
<212> TYPE: DNA
<213> ORGANISM: Homo sapiens

<400> SEQUENCE: 45

```
gtactcgaga aaagacatgg tgatggttct ttctctgatg agatgaacac cattcttgat        60
aaccttgccg ccagagactt tatcaactgg ttgattcaga ccaagatcac tgacggtggt       120
ggtggttctg gaggaggagg atctggtcca gctggtgaac aggtccatc tggtcctgct        180
ggagaacctg gtccttctgg accagctgga gagccaggtc cttcaggccc tgctggtgaa       240
cctggccctt ctgggccagc tggtgaaccc ggccctagtg agtccaaata tggtccccca       300
tgcccacctt gcccagcacc tgagttcctg ggaggaccat cagtctttct gttcccccca       360
aaacccaagg atactttgat gatttccaga actcctgaag ttacttgtgt tgtggttgat       420
gtctctcaag aggacccaga agttcaattt aactggtacg ttgatggtgt tgaagttcat       480
aacgctaaga ctaagccaag agaagaacaa tttgcttcta cttacagagt tgtttctgtt       540
ttgactgttt tgcatcaaga ttggttgaac ggtaaggaat acaagtgtaa ggtctccaac       600
aaaggccttc cgtcctccat cgagaaaacc atctccaagg ctaagggtca accaagagaa       660
ccacaagttt acactttgcc accatctcaa gaagaaatga ctaagaacca agtttctttg       720
acttgtttgg ttaagggttt ttacccatct gacattgctg ttgaatggga atctaacggt       780
caaccagaaa acaactataa gactactcca ccagttttgg attctgatgg ttctttcttc       840
ttgtactcca gattgactgt tgacaagtca agatggcagg agggaaatgt cttctcatgc       900
tccgtgatgc atgaggctct gcacaaccac tacacacaga gagtctttc cctgtcttta       960
ggttaatagg aattccggt                                                    979
```

<210> SEQ ID NO 46
<211> LENGTH: 1024
<212> TYPE: DNA
<213> ORGANISM: Homo sapiens

<400> SEQUENCE: 46

```
gtactcgaga aaagacatgg tgatggttct ttctctgatg agatgaacac cattcttgat      60
aaccttgccg ccagagactt tatcaactgg ttgattcaga ccaagatcac tgacggtggt     120
ggtggttctg gaggaggagg atctggtcct cctggtcctg ctggtcctcc tggtcctgct     180
ggtcctcctg tcctgctggg accaccagga ccagccggac caccaggacc agccgggccc     240
ccaggtcctg ctggtcctcc tggtcctgct ggtcctcctg tcctgctggg accaccagga     300
ccagccggac caccaggacc agccgagtcc aaatatggtc cccatgcccc accttgccca     360
gcacctgagt tcctgggagg accatcagtc tttctgttcc ccccaaaacc caaggatact     420
ttgatgattt ccagaactcc tgaagttact tgtgttgtgg ttgatgtctc tcaagaggac     480
ccagaagttc aatttaactg gtacgttgat ggtgttgaag ttcataacgc taagactaag     540
ccaagagaag aacaatttgc ttctacttac agagttgttt ctgttttgac tgttttgcat     600
caagattggt tgaacggtaa ggaatacaag tgtaaggtct ccaacaaagg ccttccgtcc     660
tccatcgaga aaaccatctc aaggctaagg gtcaaccaa gagaaccaca agtttacact     720
ttgccaccat ctcaagaaga atgactaag aaccaagttt ctttgacttg tttggttaag     780
ggttttttacc catctgacat tgctgttgaa tgggaatcta acggtcaacc agaaaacaac     840
tataagacta ctccaccagt tttggattct gatggttctt tcttcttgta ctccagattg     900
actgttgaca gtcaagatg gcaggaggga atgtcttct catgctccgt gatgcatgag     960
gctctgcaca accactacac acagaagagt ctttccctgt ctttaggtta ataggaattc    1020
cggt                                                                 1024
```

<210> SEQ ID NO 47
<211> LENGTH: 841
<212> TYPE: DNA
<213> ORGANISM: Homo sapiens

<400> SEQUENCE: 47

```
gtactcgaga aaagacatgg tgatggttct ttctctgatg agatgaacac cattcttgat      60
aaccttgccg ccagagactt tatcaactgg ttgattcaga ccaagatcac tgacccttct     120
tctggtgctc caccaccatc tgagtccaaa tatggtcccc catgcccacc ttgcccagca     180
cctgagttcc tgggaggacc atcagtcttt ctgttccccc caaaacccaa ggatactttg     240
atgatttcca gaactcctga agttactgt gttgtggttg atgtctctca agaggaccca     300
gaagttcaat ttaactggta cgttgatggt gttgaagttc ataacgctaa gactaagcca     360
agagaagaac aatttgcttc tacttacaga gttgtttctg ttttgactgt tttgcatcaa     420
gattggttga acggtaagga atacaagtgt aaggtctcca acaaaggcct tccgtcctcc     480
atcgagaaaa ccatctccaa ggctaagggt caaccaagag aaccacaagt ttacactttg     540
ccaccatctc aagaagaaat gactaagaac caagtttctt tgacttgttt ggttaagggt     600
ttttacccat ctgacattgc tgttgaatgg gaatctaacg tcaaccaga aaacaactat     660
aagactactc caccagtttt ggattctgat ggttcttttct tcttgtactc cagattgact     720
gttgacaagt caagatggca ggagggaaat gtcttctcat gctccgtgat gcatgaggct     780
```

```
ctgcacaacc actacacaca gaagagtctt tccctgtctt taggttaata ggaattccgg    840
t                                                                   841
```

<210> SEQ ID NO 48
<211> LENGTH: 811
<212> TYPE: DNA
<213> ORGANISM: Homo sapiens

<400> SEQUENCE: 48

```
gtactcgaga aaagacatgg tgatggttct ttctctgatg agatgaacac cattcttgat     60
aaccttgccg ccagagactt tatcaactgg ttgattggtg gtggtggttc tgagtccaaa    120
tatggtcccc catgcccacc ttgcccagca cctgagttcc tgggaggacc atcagtcttt    180
ctgttccccc caaacccaa ggatactttg atgatttcca gaactcctga agttacttgt     240
gttgtggttg atgtctctca agaggaccca gaagttcaat ttaactggta cgttgatggt    300
gttgaagttc ataacgctaa gactaagcca agagaagaac aatttgcttc tacttacaga    360
gttgtttctg ttttgactgt tttgcatcaa gattggttga cggtaagga atacaagtgt     420
aaggtctcca acaaaggcct tccgtcctcc atcgagaaaa ccatctccaa ggctaagggt    480
caaccaagag aaccacaagt ttacactttg ccaccatctc aagaagaaat gactaagaac    540
caagtttctt tgacttgttt ggttaagggt ttttacccat ctgacattgc tgttgaatgg    600
gaatctaacg gtcaaccaga aaacaactat aagactactc caccagtttt ggattctgat    660
ggttctttct tcttgtactc cagattgact gttgacaagt caagatggca ggagggaaat    720
gtcttctcat gctccgtgat gcatgaggct ctgcacaacc actacacaca gaagagtctt    780
tccctgtctt taggttaata ggaattccgg t                                   811
```

<210> SEQ ID NO 49
<211> LENGTH: 835
<212> TYPE: DNA
<213> ORGANISM: Homo sapiens

<400> SEQUENCE: 49

```
gtactcgaga aaagacatgg tgatggttct ttctctgatg agatgaacac cattcttgat     60
aaccttgccg ccagagactt tatcaactgg ttgattcaga ccaagggtgg tggtggttct    120
ggaggaggag gatctgagtc caaatatggt ccccatgcc accttgccc agcacctgag     180
ttcctgggag gaccatcagt cttctgttc cccccaaaac caaggatac tttgatgatt     240
ccagaactc ctgaagttac ttgtgttgtg gttgatgtct ctcaagagga cccagaagtt    300
caatttaact ggtacgttga tggtgttgaa gttcataacg ctaagactaa gccaagagaa    360
gaacaatttg cttctactta cagagttgtt tctgttttga ctgttttgca tcaagattgg    420
ttgacggta aggaatacaa gtgtaaggtc tccaacaaag gccttccgtc ctccatcgag    480
aaaaccatct ccaaggctaa gggtcaacca agagaaccac aagtttacac tttgccacca    540
tctcaagaag aaatgactaa gaaccaagtt tctttgactt gtttggttaa gggtttttac    600
ccatctgaca ttgctgttga atgggaatct aacggtcaac cagaaaacaa ctataagact    660
actccaccag ttttggattc tgatggttct ttcttcttgt actccagatt gactgttgac    720
aagtcaagat ggcaggaggg aaatgtcttc tcatgctccg tgatgcatga ggctctgcac    780
aaccactaca cacagaagag tctttcccctg tctttaggtt aataggaatt ccggt         835
```

<210> SEQ ID NO 50
<211> LENGTH: 838

<212> TYPE: DNA
<213> ORGANISM: Homo sapiens

<400> SEQUENCE: 50

```
gtactcgaga aaagacatgg tgatggttct ttctctgatg agatgaacac cattcttgat     60
aaccttgccg ccagagactt tatcaactgg ttgattcctt cttctggtgc tccaccacca    120
tctggtggtg gtggttctga gtccaaatat ggtcccccat gcccaccttg cccagcacct    180
gagttcctgg gaggaccatc agtctttctg ttccccccaa aacccaagga tactttgatg    240
atttccagaa ctcctgaagt tacttgtgtt gtggttgatg tctctcaaga ggacccagaa    300
gttcaattta actggtacgt tgatggtgtt gaagttcata cgctaagac taagccaaga    360
gaagaacaat ttgcttctac ttacagagtt gtttctgttt tgactgtttt gcatcaagat    420
tggttgaacg gtaaggaata caagtgtaag gtctccaaca aaggccttcc gtcctccatc    480
gagaaaacca tctccaaggc taagggtcaa ccaagagaac acaagtttta cactttgcca    540
ccatctcaag aagaaatgac taagaaccaa gtttctttga cttgtttggt taagggtttt    600
tacccatctg acattgctgt tgaatgggaa tctaacggtc aaccagaaaa caactataag    660
actactccac cagttttgga ttctgatggt tctttcttct tgtactccag attgactgtt    720
gacaagtcaa gatggcagga gggaaatgtc ttctcatgct ccgtgatgca tgaggctctg    780
cacaaccact acacacagaa gagtctttcc ctgtctttag gttaatagga attccggt     838
```

<210> SEQ ID NO 51
<211> LENGTH: 871
<212> TYPE: DNA
<213> ORGANISM: Homo sapiens

<400> SEQUENCE: 51

```
gtactcgaga aaagacatgg tgatggttct ttctctgatg agatgaacac cattcttgat     60
aaccttgccg ccagagactt tatcaactgg ttgattcaga ccaagaacgg aggaccttct    120
tctggtgctc caccaccatc tggtggtggt ggttctggag gaggaggatc tgagtccaaa    180
tatggtcccc catgcccacc ttgcccagca cctgagttcc tgggaggacc atcagtcttt    240
ctgttccccc caaaacccaa ggatactttg atgatttcca gaactcctga agttacttgt    300
gttgtggttg atgtctctca agaggaccca gaagttcaat ttaactggta cgttgatggt    360
gttgaagttc ataacgctaa gactaagcca agagaagaac aatttgcttc tacttacaga    420
gttgtttctg ttttgactgt tttgcatcaa gattggttga acggtaagga atacaagtgt    480
aaggtctcca acaaaggcct tccgtcctcc atcgagaaaa ccatctccaa ggctaagggt    540
caaccaagag aaccacaagt ttacactttg ccaccatctc aagaagaaat gactaagaac    600
caagtttctt tgacttgttt ggttaagggt ttttacccat ctgacattgc tgttgaatgg    660
gaatctaacg gtcaaccaga aaacaactat aagactactc caccagtttt ggattctgat    720
ggttcttttct tcttgtactc cagattgact gttgacaagt caagatggca gggagggaaat    780
gtcttctcat gctccgtgat gcatgaggct ctgcacaacc actacacaca gaagagtctt    840
tccctgtctt taggttaata ggaattccgg t                                    871
```

<210> SEQ ID NO 52
<211> LENGTH: 865
<212> TYPE: DNA
<213> ORGANISM: Homo sapiens

<400> SEQUENCE: 52

```
gtactcgaga aaagacatgg tgatggttct ttctctgatg agatgaacac cattcttgat      60
aaccttgccg ccagagactt tatcaactgg ttgattaacg gaggaccttc ttctggtgct     120
ccaccaccat ctggtggtgg tggttctgga ccagctggac caaatgagtc caaatatggt     180
cccccatgcc caccttgccc agcacctgag ttcctgggag gaccatcagt ctttctgttc     240
cccccaaaac ccaaggatac tttgatgatt ccagaactc ctgaagttac ttgtgttgtg      300
gttgatgtct ctcaagagga cccagaagtt caatttaact ggtacgttga tggtgttgaa     360
gttcataacg ctaagactaa gccaagagaa gaacaatttg cttctactta cagagttgtt     420
tctgttttga ctgttttgca tcaagattgg ttgaacggta aggaatacaa gtgtaaggtc     480
tccaacaaag gccttccgtc ctccatcgag aaaaccatct ccaaggctaa gggtcaacca     540
agagaaccac aagtttacac tttgccacca ctctcaagaag aaatgactaa gaaccaagtt    600
tctttgactt gtttggttaa gggttttac ccatctgaca ttgctgttga atgggaatct      660
aacggtcaac cagaaaacaa ctataagact actccaccag ttttggattc tgatggttct    720
ttcttcttgt actccagatt gactgttgac aagtcaagat ggcaggaggg aaatgtcttc    780
tcatgctccg tgatgcatga ggctctgcac aaccactaca cacagaagag ctttccctg      840 tctttaggtt aataggaatt ccggt                                            865

<210> SEQ ID NO 53
<211> LENGTH: 856
<212> TYPE: DNA
<213> ORGANISM: Homo sapiens

<400> SEQUENCE: 53
gtactcgaga aaagacatgg tgatggttct ttctctgatg agatgaacac cattcttgat      60
aaccttgccg ccagagactt tatcaactgg ttgattcaga ccaagccttc ttctggtgct     120
ccaccaccat ctggtggtgg tggttctgga ccagctgagt ccaaatatgg tccccccatgc   180 ccaccttgcc cagcacctga gttcctggga ggaccatcag tctttctgtt ccccccaaaa    240
cccaaggata ctttgatgat tccagaactc ctgaagttac ttgtgttgt ggttgatgtc    300 tctcaagagg acccagaagt tcaatttaac tggtacgttg atggtgttga agttcataac    360
gctaagacta agccaagaga agaacaattt gcttctactt acagagttgt ttctgttttg    420
actgttttgc atcaagattg gttgaacggt aaggaataca gtgtaaggt ctccaacaaa    480 ggccttccgt cctccatcga gaaaaccatc tccaaggcta agggtcaacc aagagaacca    540
caagtttaca ctttgccacc atctcaagaa gaaatgacta gaaccaagt tctttgact    600 tgtttggtta agggttttta cccatctgac attgctgttg aatgggaatc taacggtcaa    660
ccagaaaaca actataagac tactccacca gttttggatt ctgatggttc tttcttcttg    720
tactccagat tgactgttga caagtcaaga tggcaggagg gaaatgtctt ctcatgctcc    780
gtgatgcatg aggctctgca caaccactac acacagaaga gtctttccct gtctttaggt    840
taataggaat tccggt                                                      856

<210> SEQ ID NO 54
<211> LENGTH: 36
<212> TYPE: DNA
<213> ORGANISM: Homo sapiens

<400> SEQUENCE: 54
gtactcgaga aaagacatgg tgatggttct ttctct                                36
```

<210> SEQ ID NO 55
<211> LENGTH: 36
<212> TYPE: DNA
<213> ORGANISM: Homo sapiens

<400> SEQUENCE: 55
gggaccatat ttggactcgt cagtgatctt ggtctg                                36

<210> SEQ ID NO 56
<211> LENGTH: 18
<212> TYPE: DNA
<213> ORGANISM: Homo sapiens

<400> SEQUENCE: 56
gagtccaaat atggtccc                                                    18

<210> SEQ ID NO 57
<211> LENGTH: 37
<212> TYPE: DNA
<213> ORGANISM: Homo sapiens

<400> SEQUENCE: 57
accggaattc ctattaacct aaagacaggg aaagact                               37

<210> SEQ ID NO 58
<211> LENGTH: 33
<212> TYPE: DNA
<213> ORGANISM: Homo sapiens

<400> SEQUENCE: 58
agaaccacca ccaccgtcag tgatcttggt ctg                                   33

<210> SEQ ID NO 59
<211> LENGTH: 33
<212> TYPE: DNA
<213> ORGANISM: Homo sapiens

<400> SEQUENCE: 59
ggtggtggtg gttctgagtc caaatatggt ccc                                   33

<210> SEQ ID NO 60
<211> LENGTH: 48
<212> TYPE: DNA
<213> ORGANISM: Homo sapiens

<400> SEQUENCE: 60
agatcctcct cctccagaac caccaccacc gtcagtgatc ttggtctg                   48

<210> SEQ ID NO 61
<211> LENGTH: 48
<212> TYPE: DNA
<213> ORGANISM: Homo sapiens

<400> SEQUENCE: 61
ggaggaggag gatctggcgg cggcggcagt gagtccaaat atggtccc                   48

<210> SEQ ID NO 62
<211> LENGTH: 42
<212> TYPE: DNA
<213> ORGANISM: Homo sapiens

<400> SEQUENCE: 62
ggtggtggtg gttctggacc tgctgagtcc aaatatggtc cc                         42

<210> SEQ ID NO 63
<211> LENGTH: 39
<212> TYPE: DNA
<213> ORGANISM: Homo sapiens

<400> SEQUENCE: 63
ggaggaggat ctggacctca agacaaaact cacacatgc                                    39

<210> SEQ ID NO 64
<211> LENGTH: 36
<212> TYPE: DNA
<213> ORGANISM: Homo sapiens

<400> SEQUENCE: 64
ctagaattcc tattaacccg gagacaggga gagaga                                       36

<210> SEQ ID NO 65
<211> LENGTH: 54
<212> TYPE: DNA
<213> ORGANISM: Homo sapiens

<400> SEQUENCE: 65
ggaggaggat ctggcggcgg cggcagtgga cctgctgagt ccaaatatgg tccc                   54

<210> SEQ ID NO 66
<211> LENGTH: 57
<212> TYPE: DNA
<213> ORGANISM: Homo sapiens

<400> SEQUENCE: 66
tctggaggag gaggatctgg cggcggcggc agtggtggag gcgggtctgg cggaggt               57

<210> SEQ ID NO 67
<211> LENGTH: 48
<212> TYPE: DNA
<213> ORGANISM: Homo sapiens

<400> SEQUENCE: 67
gggtctggcg gaggtggtag tggacctgat gagtccaaat atggtccc                          48

<210> SEQ ID NO 68
<211> LENGTH: 51
<212> TYPE: DNA
<213> ORGANISM: Homo sapiens

<400> SEQUENCE: 68
ggaggaggag gatctggccc accaggacct gctgagtcca aatatggtcc c                      51

<210> SEQ ID NO 69
<211> LENGTH: 57
<212> TYPE: DNA
<213> ORGANISM: Homo sapiens

<400> SEQUENCE: 69
tctggaggag gaggatctgg cccaccagga cctgctgaca aaactcacac atgccca               57

<210> SEQ ID NO 70
<211> LENGTH: 63
<212> TYPE: DNA
<213> ORGANISM: Homo sapiens

<400> SEQUENCE: 70
tctggaggag gaggatctgg tccagaaggt gctccaggtc catctgagtc caaatatggt            60
ccc                                                                              63

<210> SEQ ID NO 71
<211> LENGTH: 54
<212> TYPE: DNA
<213> ORGANISM: Homo sapiens

<400> SEQUENCE: 71
tctggaggag gaggatctgg tccatctggt gctccaggtc caccaggtcc agaa          54

<210> SEQ ID NO 72
<211> LENGTH: 45
<212> TYPE: DNA
<213> ORGANISM: Homo sapiens

<400> SEQUENCE: 72
ggtccaccag gtccagaagg tccagctgag tccaaatatg gtccc                    45

<210> SEQ ID NO 73
<211> LENGTH: 54
<212> TYPE: DNA
<213> ORGANISM: Homo sapiens

<400> SEQUENCE: 73
tctggaggag gaggatctgg tccatctggt gctccaggtc caccaggacc ttcc          54

<210> SEQ ID NO 74
<211> LENGTH: 57
<212> TYPE: DNA
<213> ORGANISM: Homo sapiens

<400> SEQUENCE: 74
gccgggggct ccggaaggac caggaggacc aggggctccg gaaggtcctg gtggacc       57

<210> SEQ ID NO 75
<211> LENGTH: 42
<212> TYPE: DNA
<213> ORGANISM: Homo sapiens

<400> SEQUENCE: 75
ccttccggag cccccggccc gcctgagtcc aaatatggtc cc                       42

<210> SEQ ID NO 76
<211> LENGTH: 57
<212> TYPE: DNA
<213> ORGANISM: Homo sapiens

<400> SEQUENCE: 76
tctggaggag gaggatctgg tccagctggt gaaccaggtc catctggtcc tgctgga       57

<210> SEQ ID NO 77
<211> LENGTH: 57
<212> TYPE: DNA
<213> ORGANISM: Homo sapiens

<400> SEQUENCE: 77
aggacctggc tctccagctg gtccagaagg accaggttct ccagcaggac cagatgg       57

<210> SEQ ID NO 78
<211> LENGTH: 57
<212> TYPE: DNA
<213> ORGANISM: Homo sapiens

<400> SEQUENCE: 78
gctggagagc caggtccttc aggccctgct ggtgaacctg gcccttctgg gccagct    57

<210> SEQ ID NO 79
<211> LENGTH: 54
<212> TYPE: DNA
<213> ORGANISM: Homo sapiens

<400> SEQUENCE: 79
gggaccatat ttggactcac tagggccggg ttcaccagct ggcccagaag ggcc    54

<210> SEQ ID NO 80
<211> LENGTH: 18
<212> TYPE: DNA
<213> ORGANISM: Homo sapiens

<400> SEQUENCE: 80
gagtccaaat atggtccc    18

<210> SEQ ID NO 81
<211> LENGTH: 57
<212> TYPE: DNA
<213> ORGANISM: Homo sapiens

<400> SEQUENCE: 81
aggaggacca gatcctcctc ctccagaacc accaccaccg tcagtgatct tggtctg    57

<210> SEQ ID NO 82
<211> LENGTH: 69
<212> TYPE: DNA
<213> ORGANISM: Homo sapiens

<400> SEQUENCE: 82
ggatctggtc ctcctggtcc tgctggtcct cctggtcctg ctggtcctcc tggtcctgct    60
ggaccacca    69

<210> SEQ ID NO 83
<211> LENGTH: 59
<212> TYPE: DNA
<213> ORGANISM: Homo sapiens

<400> SEQUENCE: 83
gcaggacctg ggggcccggc tggtcctggt ggtccggctg gtcctggtgg tccagcagg    59

<210> SEQ ID NO 84
<211> LENGTH: 59
<212> TYPE: DNA
<213> ORGANISM: Homo sapiens

<400> SEQUENCE: 84
gcccccaggt cctgctggtc ctcctggtcc tgctggtcct cctggtcctg ctggaccac    59

<210> SEQ ID NO 85
<211> LENGTH: 59
<212> TYPE: DNA
<213> ORGANISM: Homo sapiens

<400> SEQUENCE: 85
accatatttg gactcggctg gtcctggtgg tccggctggt cctggtggtc cagcaggac    59

<210> SEQ ID NO 86
<211> LENGTH: 59

```
<212> TYPE: DNA
<213> ORGANISM: Homo sapiens

<400> SEQUENCE: 86
gaccatattt ggactcagat ggtggtggag caccagaaga agggtcagtg atcttggtc      59

<210> SEQ ID NO 87
<211> LENGTH: 51
<212> TYPE: DNA
<213> ORGANISM: Homo sapiens

<400> SEQUENCE: 87
gggaccatat ttggactcag aaccaccacc accaatcaac cagttgataa a              51

<210> SEQ ID NO 88
<211> LENGTH: 48
<212> TYPE: DNA
<213> ORGANISM: Homo sapiens

<400> SEQUENCE: 88
agatcctcct cctccagaac caccaccacc cttggtctga atcaacca                  48

<210> SEQ ID NO 89
<211> LENGTH: 36
<212> TYPE: DNA
<213> ORGANISM: Homo sapiens

<400> SEQUENCE: 89
tctggaggag gaggatctga gtccaaatat ggtccc                               36

<210> SEQ ID NO 90
<211> LENGTH: 59
<212> TYPE: DNA
<213> ORGANISM: Homo sapiens

<400> SEQUENCE: 90
cagaaccacc accaccagat ggtggtggag caccagaaga aggaatcaac cagttgata      59

<210> SEQ ID NO 91
<211> LENGTH: 36
<212> TYPE: DNA
<213> ORGANISM: Homo sapiens

<400> SEQUENCE: 91
tctggtggtg gtggttctga gtccaaatat ggtccc                               36

<210> SEQ ID NO 92
<211> LENGTH: 59
<212> TYPE: DNA
<213> ORGANISM: Homo sapiens

<400> SEQUENCE: 92
ccaccagatg gtggtggagc accagaagaa ggtcctccgt tcttggtctg aatcaacca      59

<210> SEQ ID NO 93
<211> LENGTH: 59
<212> TYPE: DNA
<213> ORGANISM: Homo sapiens

<400> SEQUENCE: 93
ccaccaccat ctggtggtgg tggttctgga ggaggaggat ctgagtccaa atatggtcc      59

<210> SEQ ID NO 94
```

```
<211> LENGTH: 59
<212> TYPE: DNA
<213> ORGANISM: Homo sapiens

<400> SEQUENCE: 94
caccaccaga tggtggtgga gcaccagaag aaggtcctcc gttaatcaac cagttgata      59

<210> SEQ ID NO 95
<211> LENGTH: 59
<212> TYPE: DNA
<213> ORGANISM: Homo sapiens

<400> SEQUENCE: 95
ccaccatctg gtggtggtgg ttctggacca gctggaccaa atgagtccaa atatggtcc      59

<210> SEQ ID NO 96
<211> LENGTH: 58
<212> TYPE: DNA
<213> ORGANISM: Homo sapiens

<400> SEQUENCE: 96
agaaccacca ccaccagatg gtggtggagc accagaagaa ggcttggtct gaatcaac       58

<210> SEQ ID NO 97
<211> LENGTH: 45
<212> TYPE: DNA
<213> ORGANISM: Homo sapiens

<400> SEQUENCE: 97
tctggtggtg gtggttctgg accagctgag tccaaatatg gtccc                     45

<210> SEQ ID NO 98
<211> LENGTH: 5
<212> TYPE: PRT
<213> ORGANISM: Homo sapiens

<400> SEQUENCE: 98

Gly Gly Gly Gly Ser
1               5

<210> SEQ ID NO 99
<211> LENGTH: 6
<212> TYPE: PRT
<213> ORGANISM: Homo sapiens

<400> SEQUENCE: 99

Gly Gly Gly Gly Gly Ser
1               5

<210> SEQ ID NO 100
<211> LENGTH: 10
<212> TYPE: PRT
<213> ORGANISM: Homo sapiens

<400> SEQUENCE: 100

Gly Gly Gly Gly Ser Gly Gly Gly Gly Ser
1               5                   10

<210> SEQ ID NO 101
<211> LENGTH: 33
<212> TYPE: PRT
<213> ORGANISM: Homo sapiens

<400> SEQUENCE: 101
```

```
His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

FUSION PROTEIN FOR TREATING INTESTINAL DISEASES

CROSS REFERENCE TO RELATED PATENT APPLICATION

The present application is the US national stage of PCT/CN2017/106727 filed on Oct. 18, 2017 which claims the priority of the Chinese patent application No. CN2016109570194 filed on Oct. 27, 2016, which application is incorporated herein by reference.

FIELD OF THE INVENTION

The invention relates to the field of bio-pharmaceutical technology, and in particular to a fusion protein for treating an intestinal disease.

BACKGROUND OF THE INVENTION

Glucagon-like peptide 2 (GLP-2), a 33 amino acid polypeptide with a molecular weight of about 3.9 KD, is formed by transcription and post-translational processing of the proglucagon gene. GLP-2 is an intestinal hormone secreted by intestinal enteroendocrine L-cells after food ingestion. It's a product derived from enzymatic digestion of proglucagon by proglucagon prohormone convertase 1/3. Some brain nerve cells also secrete GLP-2. GLP-2 promotes the normal growth and development of small intestine by acting on a specific G protein-coupled receptor (GLP-2 receptor) in gut. Studies have shown that GLP-2 can protect and repair the intestinal mucosa damaged by various intestinal diseases, and increase vascularization to the intestine. It has promising trend in the clinical application of intestinal mucosa injury caused by tumor chemoradiotherapy, severe trauma (burn), total parenteral nutrition or inflammatory bowel disease, and of hemorrhagic shock, extensive enterectomy, small intestine transplantation, etc as well.

Native GLP-2 is highly susceptible to enzymatic degradation in vivo to become inactivated, and to renal clearance due to its small molecular weight. It has a short half-life of about seven minutes in human circulation due to rapid proteolytic degradation by dipeptidyl peptidase IV (DPP-IV) at the second amino acid residue (Ala-2) to form slightly active GLP-2(3-33) with 31 amino acid residues, or due to complete inactivation by endopeptidases. Teduglutide (trade name: Gattex®), a DPP-IV resistant GLP-2 analog developed by NPS Pharmaceuticals, Inc is now on market of the United States. Teduglutide is a GLP-2 variant with A2G substitution and is subcutaneously injected at a dose of 0.05 mg/kg once a day for the treatment of adults with short bowel syndrome (SBS) dependent on parenteral support (PS) (Clin Drug Investig. Teduglutide: a guide to its use in short bowel syndrome. 2015: 35 (5): 335-40).

Despite of approval, a drawback of Teduglutide is that it needs to be subcutaneously injected once a day. Moreover, although the substitution of Ala-2 by Gly results in improved DPP-IV resistance, it does not confer significant improvement on endopeptidase-mediated degradation. Therefore, half-life extension strategies should be applied to small peptide of GLP-2 to increase its in vivo exposure. However, for small peptides as GLP-2, conventional half-life extending approaches, such as fusions with human serum albumin (HSA), transferrin, or human immunoglobulin Fc fragment, do not give desired results usually because they cannot protect these peptides from endogenous protease-mediated degradation. Site-directed mutagenesis is frequently used to replace the protease-sensitive amino acids by other amino acids. An alternative is chemical modification like Liraglutide (trade name: Victoza®) developed by Novo Nordisk A/S. The cross-linked fatty acid (palmitic acid) helps prevent the GLP-1 moiety from degradation and prolong the plasma half-life by binding to human serum albumin.

In conclusion, to obtain a stable GLP-2 analog with resistance to protease-mediated degradation, fusion to long-acting carrier proteins or cross-linking with macromolecular polymers like PEGs is a reasonable solution so far. However, activity loss resulted from fusion with long-acting carrier proteins becomes the most significant defect. A flexible linker (such as short peptide comprising Gly and Ser) is usually adopted to alleviate the activity loss. However, introduction of linker is not always feasible, and risk of proteolysis may also increases by simply extending its length. Thus, it is in critical needs to obtain a long acting GLP-2R agonist, with minimal activity loss and proteolysis resistant peptide linker, as well as with improved pharmacokinetics and pharmacodynamics profiles.

SUMMARY OF THE INVENTION

Definition of Terms

"Glucagon-like peptide 2 (GLP-2)" refers to a hormone secreted by some intestinal enteroendocrine cells (L-cells) and obtained by the processing of proglucagon in vivo. Besides the gut, the brain secretes GLP-2 too, which is thought to possibly play a role in food intake controlling. GLP-2 exhibits effects on intestinal diseases as well as injury treatment and prevention, by binding to GLP-2 receptors. GLP-2 consists of 33 amino acids. Native GLP-2 has the following amino acid sequence:

```
GLP-2 (1-33)
                                    (SEQ ID NO: 1)
HADGSFSDEMNTILDNLAARDFINWLIQTKITD.
```

The GLP-2 receptor agonist includes native GLP-2, GLP-2 derivatives or mutants in this invention.

In this invention, the "GLP-2 receptor agonist" refers to a polypeptide able to bind to and activate GLP-2 receptor. The biological activities of the GLP-2 receptor agonists should be physiologically identical or similar to those of the native GLP-2.

The "GLP-2 derivative" or the "GLP-2 mutant" herein may be interchangeable, and refers to a polypeptide that shares at least 80% amino acid sequence identity with the native GLP-2, and has physiological activities identical or similar to those of the native GLP-2, where some amino acid residues may even be chemically modified by α-methylation, α-hydroxylation or deamination, and so on. Preferably, a GLP-2 derivative according to the invention can be obtained by N-terminal amino acid substitution, C-terminal amino acid insertion, deletion or peptide modification. The inserted or substituted amino acids may be native L-amino acids or a non-native D-amino acid.

"Long-acting carrier protein" according to the invention refers to a protein able to prolong the half lives of active proteins in vivo while showing undetectable or negligible biological function itself. Frequently used long-acting carrier proteins include but not limited to: fragment crystallizable region of an immunoglobulin (IgG), human serum albumin or transferrin, etc. Polyethylene glycol (PEG) is another common option used for half life extension.

"Immunoglobulin" (IgG) refers to a kind of proteins that take part in the protective immunity of an organism by selectively targeting an antigen. An immunoglobulin is composed of two identical light chains and two identical heavy chains. Light chain and heavy chain both contains variable region and constant region. There are two kinds of light chains: κ light chain and λ light chain (Coleman et al., Fundamental Immunology, second edition, 1989, 55-73) based on the differences of amino acid sequences in the constant regions. The immunoglobulin is classified into five isotypes: IgG, IgA, IgD, IgE and IgM. IgG can be divided into four subtypes, including IgG1, IgG2, IgG3 and IgG4, based on individual characteristics on the constant domain of heavy chain. IgG1 and IgG4 are the most widely used isotypes of monoclonal antibody therapeutics at present because of their high affinity to FcRn for recycling, which results in a long half life (about 21 days on average).

"Fc mutant": the Fc mutant herein refers to a mutant formed by substituting or inserting specific amino acids in constant domains of Fc fragments derived from natural human or other mammalian IgGs. The mutation does not break the FcRn binding, and thus has minimal effect on these Fc mutants as long-acting carrier proteins.

In order to overcome the existing technical defects, the invention provides a fusion protein presented in the following structure:

R-L-P   Formula I wherein
R is a GLP-2 receptor agonist;
P is a long-acting carrier protein;
L is a peptide linker and is represented by the following formula:

$(XSSGAPPPS)_u$-G/S-$(G-W_1-W_2)_m$   Formula II wherein
X is selected from the group consisting of P, GP, GGP and NGGP;
G/S is a peptide consisting of G and S in arbitrary combination and with 5 to 25 amino acids in length;
$W_1$ and $W_2$ are selected from the group of 19 natural amino acid residues except Cys, respectively;
u is either 0 or 1;
m is an integer of 1 to 20.

In Formula I, R is a GLP-2 receptor agonist including a native GLP-2 or GLP-2 derivatives. GLP-2 derivatives include GLP-2 mutants obtained by amino acid substitution, deletion, insertion or modification of a native GLP-2 sequence, non-natural amino acid substitution or the like. Preferably, the GLP-2 receptor agonist is a mutant (SEQ ID NO:2) formed by substituting Ala-2 of a native GLP-2 sequence (SEQ ID NO:1) with Gly. According to the invention, the GLP-2 receptor agonist may also be selected from GLP-2 mutants formed by substituting Ala-2 of a native GLP-2 sequence with Gly and deleting C-terminal 1-6 amino acid residues, such as SEQ ID NO:3 and SEQ ID NO:4. In one embodiment of the invention, the GLP-2 receptor agonist is a mutant (SEQ ID NO:2) formed by substituting Ala-2 with Gly; In another embodiment, the GLP-2 receptor agonist is a GLP-2 mutant (SEQ ID NO:4) formed by substituting Ala-2 with Gly and deleting C-terminal 6 amino acid residues. The proteins according to the invention may have various derivatives, which may be, but are not limited to, different forms of salt and modified products thereof, and the like, such as modified amino, carboxyl, hydroxyl and sulfydryl of a polypeptide.

In Formula I, the long-acting carrier protein includes, but is not limited to, a constant region Fc part of a mammal-derived immunoglobulin IgG1 or IgG4, human serum albumin and transferrin. Preferably, the long-acting carrier protein is selected from a constant region Fc part of a human immunoglobulin IgG1 (SEQ ID NO:5) or IgG4 (SEQ ID NO:6) and a mutant thereof, and more preferably, the long-acting carrier protein is selected from a constant region Fc part of a nonglycosylated N297-human immunoglobulin IgG1 and IgG4. According to one embodiment of the invention, the long-acting carrier protein is selected from a constant region Fc mutant of a human immunoglobulin IgG1 and has the sequence as shown in SEQ ID NO:7; and in another embodiment of the invention, the long-acting carrier protein is selected from a constant region Fc mutant of a human immunoglobulin IgG4 and has the sequence as shown in SEQ ID NO:8. For an IgG4 antibody, a further S228P mutation is introduced to weaken the chain exchange phenomenon characteristic of the IgG4 isotype. All of the Fc fragments can obviously extend the in vivo half lives of GLP-2 mutants.

In Formula I, L is a peptide linker used to link a GLP-2 mutant and a long-acting carrier protein. L has the following structure:

$(XSSGAPPPS)_u$-G/S-$(G-W_1-W_2)_m$   Formula II

Wherein X is selected from the group consisting of P, GP, GGP and NGGP; $W_1$ and $W_2$ are selected from the group consisting of 19 natural amino acid residues except Cys, respectively; u is 0 or 1; and m is an integer of 1 to 20. The said G/S is a peptide consisting of G and S in arbitrary combination and with 5 to 25 amino acids in length; preferably, the G/S is any one of GGGGS (SEQ ID NO:98), GGGGGS (SEQ ID NO:99) and GGGGSGGGGS (SEQ ID NO:100). Preferably, the said $W_1$ and $W_2$ are independently selected from the following amino acids: A, N, D, Q, E, K, P, S and R, respectively. More preferably, the $W_1$ and $W_2$ are independently selected from A, P, S, E, Q and D, respectively.

Preferably, said L is any one selected from SEQ ID NO:30 ((GGGGS)$_2$GPPGPA), SEQ ID NO:31 ((GGGGS)$_2$GPN-GAPGPS) and SEQ ID NO:32 ((GGGGS)$_2$GPSGAPGPPG-PEGPA).

In general, the fusion of an active protein with other proteins is very likely to significantly reduce its bioactivity, especially for a short peptide of a GLP-2 receptor agonist. This is because a small peptide is readily subjected to steric hindrance, which results in a significant activity loss.

Furthermore, N-terminal truncation of a dipeptide was reported during expression of exendin-4 (HGDGSFSDE-MNTILDNLAARDFINWLIQTKITD, SEQ ID NO:101) in yeast, which got substantial improvement after knockout of STE13 gene in yeast (Prabha L et al. Protein Expr Purif. 2009: 155-61. Identification of the dipeptidyl aminopeptidase responsible for N-terminal clipping of recombinant Exendin-4 precursor expressed in *Pichia pastoris*.). This indicates that for a GLP-2 mutant, the substitution of A2G is probably not enough to confer resistance to dipeptidyl peptidase-mediated degradation. However, the inventors found that the internal cleavage, which is far from the N-terminus, is more prominent when a GLP-2 mutant is expressed in yeast. Therefore, activity loss still exists although the N-terminus of a GLP-2 mutant remains intact after the yeast STE13 gene is knocked out, According to the invention, the introduction of G/S-$(G-W_1-W_2)_m$ significantly mitigates activity loss of the GLP-2 mutant fusion protein. A G/S sequence is a flexible peptide linker known in the art and is frequently used to link two different proteins. However, the inventors found that G/S peptide (GGGGS unit is most commonly used) alone is not enough to prevent bioactivity loss of a GLP-2 receptor agonist. After (G-$W_1$-$W_2$) addition, the longer the GGGGS unit is, the more significant activity was retained. Likewise, instead of alleviating bioactivity loss, the (G-$W_1$-$W_2$) unit alone causes greater activity loss. The inventors have found that only a combination of G/S-(G-$W_1$-$W_2$) can significantly prevent bioactivity loss of the GLP-2 mutant.

A unit XSSGAPPPS may be further added to the peptide linker according to the invention. In the present invention, fusing a sequence XSSGAPPPS to the C-terminus of a GLP-2 mutant increases the stabilities of some GLP-2 mutants without compromising their bioactivities, thereby extending the in vivo half lives. During secretory expression in *Pichia Pastoris* GS115, fusing PSSGAPPPS to a C-terminally truncated GLP-2 mutant reduced degradation and improved the expression yield.

The inventors found that compared with a GLP-2 mutant fusion protein R-P without a peptide linker, a (XSSGAPPPS)$_u$-G/S-(G-$W_1$-$W_2$)$_m$ peptide linker effectively reduces degradation and bioactivity loss of the GLP-2 mutant. u may be 0 or 1, depending on the form of the GLP-2 mutant.

Another contribution of the invention is that it eliminates the aggregation arising from fusion of GLP-2 with an Fc fragment. For example, GLP-2 MIMETIBODY™ is readily subjected to noncovalent dimerization (Baker A E et al. The dimerization of glucagon-like peptide-2 MIMETIBODY™ is linked to leucine-17 in the glucagon-like peptide-2 region. J Mol Recognit. 2012 25 (3): 155-64.). In GLP-2 MIMETIBODY™, there is also a flexible G/S peptide linker between an IgG4-Fc fragment and GLP-2 analog moiety. However, according to one embodiment of the invention, a GLP-2 mutant fusion protein with (XSSGAPPPS)$_u$-G/S-(G-$W_1$-$W_2$)$_m$ peptide linker indicated no visible aggregation in SEC-HPLC. It's thought that a possible interaction, between a specific conformation formed in the peptide linker and the hydrophobic region of the GLP-2 mutant, contributed to elimination of dimers.

In a fusion protein consisting of two different domains, the peptide linker plays an extremely important role as a spacer between these two different domains. Generally different peptide linker is used in different protein. This is because individual active protein has its own conformational structure and molecular weight. Therefore, it is necessary to optimize the peptide linker in the fusion protein. Although flexible peptide linkers consisting of G and S have been successfully applied to a variety of proteins, it is not desirable enough in the case GLP-2. In the present invention, the inventors obtained a series of peptide linker specific for GLP-2 mutants and long-acting carrier proteins by substantial screening. These peptide linkers effectively reduce activity losses of GLP-2 receptor agonists and alleviate proteolysis as well. According to the embodiments of the present invention, the following combinations of GLP-2 mutants and peptide linkers are used (Table 1).

TABLE 1

Various GLP-2 fusion proteins

| Fusion proteins SEQ ID NO: | DNA sequence SEQ ID NO: | GLP-2 mutants | peptide linkers | Long-acting carrier proteins |
| --- | --- | --- | --- | --- |
| 9 | 33 | A2G | N.A. | hIgG4/S228P, N297A |
| 10 | 34 | A2G | GGGGS | hIgG4/S228P, N297A |
| 11 | 35 | A2G | (GGGGS)$_3$ | hIgG4/S228P, N297A |
| 12 | 36 | A2G | GGGGSGPA | hIgG4/S228P, N297A |
| 13 | 37 | A2G | (GGGGS)$_2$GPQ | hIgG1/N297A |
| 14 | 38 | A2G | (GGGGS)$_3$GPA | hIgG4/S228P, N297A |
| 15 | 39 | A2G | (GGGGS)$_5$GPD | hIgG4/S228P, N297A |
| 16 | 40 | A2G | (GGGGS)$_2$GPPGPA | hIgG4/S228P, N297A |
| 17 | 41 | A2G | (GGGGS)$_2$GPPGPA | hIgG1/N297A |
| 18 | 42 | A2G | (GGGGS)$_2$GPEGAPGPS | hIgG4/S228P, N297A |
| 19 | 43 | A2G | (GGGGS)$_2$GPSGAPGPPGPEGPA | hIgG4/S228P, N297A |
| 20 | 44 | A2G | (GGGGS)$_2$(GPSGAPGPP)$_3$ | hIgG4/S228P, N297A |
| 21 | 45 | A2G | (GGGGS)$_2$(GPAGEPGPS)$_5$ | hIgG4/S228P, N297A |

TABLE 1-continued

Various GLP-2 fusion proteins

| Fusion proteins SEQ ID NO: | DNA sequence SEQ ID NO: | GLP-2 mutants | peptide linkers | Long-acting carrier proteins |
|---|---|---|---|---|
| 22 | 46 | A2G | (GGGGS)$_2$(GPPGPA)$_{10}$ | hIgG4/S228P, N297A |
| 23 | 47 | A2G | PSSGAPPPS | hIgG4/S228P, N297A |
| 24 | 48 | A2G, ΔC6 | GGGGS | hIgG4/S228P, N297A |
| 25 | 49 | A2G, ΔC3 | (GGGGS)$_2$ | hIgG4/S228P, N297A |
| 26 | 50 | A2G, ΔC6 | PSSGAPPPSGGGGS | hIgG4/S228P, N297A |
| 27 | 51 | A2G, ΔC3 | NGGPSSGAPPPS(GGGGS)$_2$ | hIgG4/S228P, N297A |
| 28 | 52 | A2G, ΔC6 | NGGPSSGAPPPSGGGGSGPAGPN | hIgG4/S228P, N297A |
| 29 | 53 | A2G, ΔC3 | PSSGAPPPSGGGGSGPA | hIgG4/S228P, N297A |

Note:
In the table above, only mutated amino acids of GLP-2 mutant sequences are indicated. For example, A2G indicates that the second amino acid A in a native GLP-2 (SEQ ID NO: 1) is replaced with G, ΔC indicates C-terminal deletion, and a number after ΔC indicates the number of amino acid deleted. For example, ΔC6 indicates a GLP-2 mutant with C-terminal 6 amino acids deleted. Similarly, only mutated amino acid of hIgG4 and hIgG1 Fc fragment mutants are indicated, and h indicates human derived.

In one aspect of the invention, there is provided a nucleotide sequence encoding the said fusion protein.

In one aspect of the present invention, there is provided a recombinant expression vector carrying a gene coding for the fusion protein according to the invention. At present, the commonly used recombinant expression vectors include, but are not limited to, eukaryotic expression vectors, such as pPIC9, pPIC9K, pPICZalpha A and pcDNA3.1, prokaryotic expression vectors, such as pET41a and pET32a, and other self-constructed plasmids having components required for expressing desired exogenous recombinant proteins, all of which can be used for the expression of the GLP-2 mutants according to the invention.

In a further aspect of the present invention, there is provided a method for expressing the fusion protein. The said method includes introducing the recombinant expression vector containing the fusion protein coding gene into a host cell to obtain the fusion protein by inducible or constitutive expression. The expression host may be yeasts, *Escherichia coli*, mammalian cells or the like, preferably yeast, more specifically, *Pichi pastoris*.

The purification of the fusion protein according to the invention includes the techniques such as salting out, precipitation, ultrafiltration, chromatography, and a combination thereof. Among them, the chromatography includes affinity chromatography, ion exchange, hydrophobic interaction, reversed phase chromatography or the like.

The protein and derivatives thereof according to the invention may be separately used or be used in the form of a pharmaceutical preparation made by adding one or more pharmaceutically acceptable auxiliary materials thereto. The auxiliary materials include conventional auxiliary materials in the pharmaceutical field, such as water, sugar, such as lactose, dextrose and alcohols, such as sorbitol, mannitol and xylitol, amino acids, etc. In addition, the pharmaceutical composition according to the invention may further include a filler, an excipient, a humectant and a bacteriostat.

The fusion protein according to the invention may be made into an injection. The formulation may be prepared according to the conventional strategies in the pharmaceutical field. The pharmaceutical preparation may exist in a container for single-dose or multi-dose use, such as an airtight ampoules or a vial. A lyophilized preparation is prepared by lyophilizing a liquid preparation, and is used after adding a sterilized and pyrogen-free liquid solvent, such as water for injection.

The fusion protein and derivatives thereof or pharmaceutical compositions thereof according to the invention can be used as intestinal protective hormones for treating patients with intestinal injury and diseases caused by tumor chemoradiotherapy, severe trauma (burn), total parenteral nutrition, or with intestinal mucosa injury caused by inflammatory bowel disease, extensive enterectomy and small intestine transplantation, etc.

The fusion protein and derivatives thereof according to the invention may be administered by intravenous injection, subcutaneous injection or the like. The therapeutic regimen includes use of a mono-dose or combination over a period.

Figure 1:
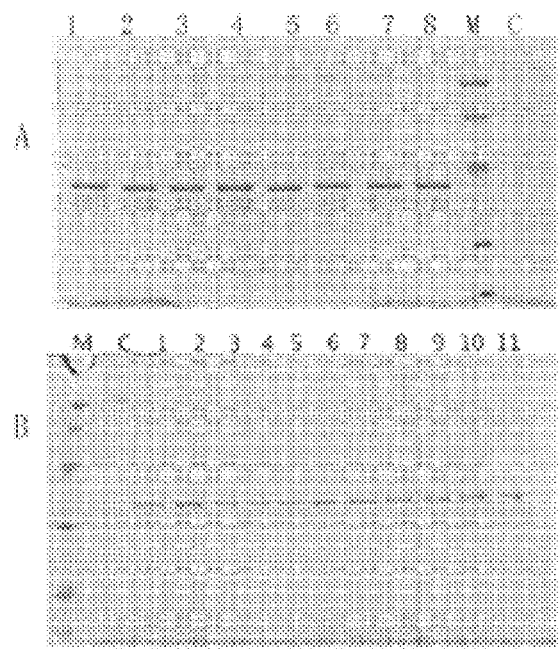
FIG. 1 shows SDS-PAGE electrophoresis result of GLP-2 mutants screening through induction. Lanes 1-8 in A are SEQ ID NO:9-11 and 23-27, respectively; lanes 1-11 in B are SEQ ID NO:12-22, respectively; all lanes in C are samples expressed in pPIC9-transformed GS115 control; and lane M is protein markers: 97, 66, 44, 29, 21 and 14 KD.

The invention is described in further detail below in conjunction with the embodiments for a more complete understanding.

DETAILED DESCRIPTION OF THE PREFERRED EMBODIMENTS

Unless otherwise stated, all of the following embodiments are well-known conventional methods to those skilled in the art. For example, a recombinant expression plasmid can be constructed based on a common molecular biology literature, such as Molecular Cloning: A Laboratory Manual, 3rd edition by Sambrook J & Russell D W, New York: Cold Spring Harbor Laboratory Press, 2001 or a technical solution in an operation manual provided by a commercial manufacturer.

Example 1: Gene Cloning and Expression Vector Construction

The coding genes for GLP-2 mutant, peptide linkers and Fc fragments of human IgG1 and IgG4 were designed according to their amino acid sequences and codon preference in yeasts as shown in Table 1, all of which were obtained through gene synthesis. Complete coding genes for a fusion protein were obtained through amplification with SOE-PCR (splicing by overlap extension, abbreviated as SOE). Those skilled in the art can easily infer the gene sequences from amino acid sequences in Table 1 and design corresponding primers for amplifications. XhoI and EcoRI recognition sites were added in termini of an upstream primer of a GLP-2 mutant gene and a downstream primer of an Fc fragment, respectively. The PCR (Polymerase Chain Reaction) products were cloned into pPIC9 vector for expression of fusion proteins of SEQ ID NO: 9-29. SEQ ID NO:2 was used as a control and obtained through chemical synthesis. Table 2 lists primer sequences for amplifying the GLP-2 mutant fusion proteins in Table 1.

TABLE 2

Primer Sequences for Amplifying GLP-2 Mutant Fusion Proteins

| SEQ ID NO: | Sequence (5'-3') |
|---|---|
| 54 | gtactcgagaaaagacatggtgatggttctttctct |
| 55 | gggaccatatttggactcgtcagtgatcttggtctg |
| 56 | gagtccaaatatggtccc |
| 57 | accggaattcctattaacctaaagacagggaaagact |
| 58 | agaaccaccaccaccgtcagtgatcttggtctg |
| 59 | ggtggtggtggttctgagtccaaatatggtccc |
| 60 | agatcctcctcctccagaaccaccaccaccgtcagtgatcttggtctg |
| 61 | ggaggaggaggatctggcggcggcggcagtgagtccaaatatggtccc |
| 62 | ggtggtggtggttctggacctgctgagtccaaatatggtccc |
| 63 | ggaggaggatctggacctcaagacaaaactcacacatgc |
| 64 | ctagaattcctattaacccggagacagggagagaga |
| 65 | ggaggaggatctggcggcggcggcagtggacctgctgagtccaaatatggtccc |
| 66 | tctggaggaggaggatctggcggcggcggcagtggtggaggcgggtctggcggaggt |
| 67 | gggtctggcggaggtggtagtggacctgatgagtccaaatatggtccc |
| 68 | ggaggaggaggatctggcccaccaggacctgctgagtccaaatatggtccc |
| 69 | tctggaggaggaggatctggcccaccaggacctgctgacaaaactcacacatgccca |
| 70 | tctggaggaggaggatctggtccagaaggtgctccaggtccatctgagtccaaatatggtccc |
| 71 | tctggaggaggaggatctggtccatctggtgctccaggtccaccaggtccagaa |
| 72 | ggtccaccaggtccagaaggtccagctgagtccaaatatggtccc |
| 73 | tctggaggaggaggatctggtccatctggtgctccaggtccaccaggaccttcc |
| 74 | gccggggctccggaaggaccaggaggaccaggggctccggaaggtcctggtggacc |
| 75 | ccttccggagccccggcccgcctgagtccaaatatggtccc |
| 76 | tctggaggaggaggatctggtccagctggtgaaccaggtccatctggtcctgctgga |
| 77 | aggacctggctctccagctggtccagaaggaccaggttctccagcaggaccagatgg |
| 78 | gctggagagccaggtccttcaggccctgctggtgaacctggccatctgggccagct |
| 79 | gggaccatatttggactcactagggccgggttcaccagctggcccagaagggcc |
| 80 | gagtccaaatatggtccc |
| 81 | aggaggaccagatcctcctcctccagaaccaccaccaccgtcagtgatcttggtctg |
| 82 | ggatctggtcctcctggtcctgctggtcctcctggtcctgctggtcctcctggtcctgctggaccacca |
| 83 | gcaggacctggggcccggctggtcctggtggtccggctggtcctggtggtccagcagg |
| 84 | gcccccaggtcctgctggtcctcctggtcctgctgtcctcctggtcctgctggaccac |
| 85 | accatatttggactcggctggtcctggtggtccggctggtcctggtggtccagcaggac |
| 86 | gaccatatttggactcagatggtggtggagcaccagaagaagggtcagtgatcttggtc |

TABLE 2-continued

Primer Sequences for Amplifying
GLP-2 Mutant Fusion Proteins

| SEQ ID NO: | Sequence (5'-3') |
|---|---|
| 87 | gggaccatatttggactcagaaccaccaccaccaa tcaaccagttgataaa |
| 88 | agatcctcctcctccagaaccaccaccacccttgg tctgaatcaacca |
| 89 | tctggaggaggaggatctgagtccaaatatggtcc c |
| 90 | cagaaccaccaccaccagatggtggtggagcacca gaagaaggaatcaaccagttgata |
| 91 | tctggtggtggtggttctgagtccaaatatggtcc c |
| 92 | ccaccagatggtggtggagcaccagaagaaggtcc tccgttcttggtctgaatcaacca |
| 93 | ccaccaccatctggtggtggtggttctggaggagg aggatctgagtccaaatatggtcc |
| 94 | caccaccagatggtggtggagcaccagaagaaggt cctccgttaatcaaccagttgata |
| 95 | ccaccatctggtggtggtggttctggaccagctgg accaaatgagtccaaatatggtcc |
| 96 | agaaccaccaccaccagatggtggtggagcaccag aagaaggcttggtctgaatcaac |
| 97 | tctggtggtggtggttctggaccagctgagtccaa atatggtccc |

PCR reaction system (50 μL): 5 μL 10×Pfu buffer, dNTP mix (200 μmol/L), upstream primer (0.5 μmol/L), downstream primer (0.5 μmol/L), 0.1 μg template, 0.5 μL Pfu DNA polymerase (5 U/μL), balanced with sterile DD H$_2$O to 50 μL. All PCR processes are as follows: pre-denaturation at 94° C. for 2 min, 27 cycles of denaturation at 94° C. for 30 sec, annealing at 58° C. for 30 sec, extension at 72° C. for 3 min and, following the final cycle, an additional extension at 72° C. for 5 min, and storage at 4° C. PCR product is detected by agarose gel electrophoresis, and the experimental results are consistent with the theoretical results.

After digested with restriction endonuclease XhoI and EcoRI, a fusion gene was ligated into yeast expression vector pPIC9 with the same digestion, (Life technologies, USA) to obtain a recombinant expression plasmid. After the recombinant plasmid had been linearized, it was transformed into *Pichia pastoris* GS115 (His) by electroporation. The transformed *Pichia pastoris* GS115 was then cultured in a screening plate medium (His⁻) at 30° C. for 3 days until single colonies appear.

Example 2: Recombinant Protein Acquisition

A single colony of the above transformed recombinant yeast was inoculated into 10 ml of BMGY liquid medium, cultured at 250 rpm at 30° C. for 24 h, and left to stand overnight. After the supernatant was discarded, 10 ml of a BMMY liquid medium containing 1% methanol was added for inducible expression at 250 rpm at 30° C. Strains with relatively high expression levels were selected as expression strains. Detailed procedures were described in the manufacturer's manual (Pichia Expression Kit. For Expression of Recombinant Proteins in *Pichia pastoris*. Catalog No. K1710-01).

As initial inoculum, high expressing clones obtained through screening were inoculated into YPD fluid medium (Yeast Extract Peptone Dextrose Medium), cultured at 220 rpm at 30° C. for 20-24 h until the OD$_{600}$ reached 10-20. The initial inoculum was inoculated into a 5 L fermentor with medium previously prepared according to *Pichia* Fermentation Process Guidelines of Life technologies (Biostat B Twin MO), and 10% of initial fermentation volume was inoculated. The fermentor was set to 30° C., pH5.0. Methanol feed started for inducible expression after glycerol was consumed. Temperature was controlled at 25° C. during methanol fed-batch phase, and the fermentation broth was harvested after 72 h induction. FIG. 1 shows the result of inducible expression.

As shown in FIG. 1A, similar to SEQ ID NO:9 without peptide linker, GLP-2 mutant fusion proteins only containing G/S flexible peptides or unit XSSGAPPPS or a combination thereof, such as SEQ ID NO:10-11 and 23-27, show minimal improvement on degradation during fermentation. However, after being linked to a unit $(G-W_1-W_2)_m$ (FIG. 1B), such as SEQ ID NO:12-22, no obvious degradation is detected during fermentation.

Example 3: Fusion Protein Extraction and Purification

Figure 2:
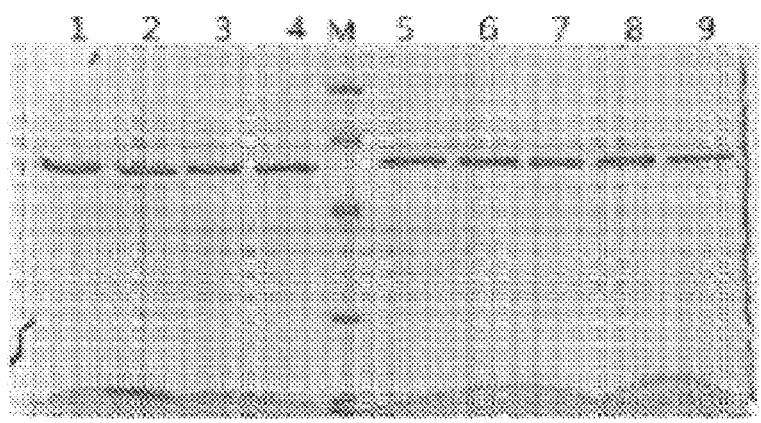
FIG. 2 shows SDS-PAGE electrophoresis result of purified GLP-2 mutants, where lanes 1-9 indicate purified samples of SEQ ID NO:12-20; and M is protein markers: 97, 66, 44, 29, 21 and 14 KD.

The fermentation broth obtained in Example 2 was centrifuged at 8000 rpm at room temperature for 30 min to collect the supernatant. Samples were loaded on a chromatographic column (Diamond Protein A BestChrome, Bestchrom (Shanghai) Biosciences Co. Ltd) pre-equilibrated with buffer solution A (0.5M NaCl, 20 mM PB, pH 7.0). The interested fusion protein bound on the column was eluted with elution buffer B (0.1M Gly-HCl, pH 3.0) after re-equilibrating with the buffer solution A. Neutralization solution (1M Tris-HCl, pH8.0), in the volume of 10% of the eluate volume, was added to adjust the pH, followed by conductivity adjustment with deionized water until the conductivity reaches 4 ms/cm or less. The adjusted eluate was then loaded on a chromatographic column (TOSOH Super Q 650-M) pre-equilibrated with buffer solution A (20 mM PB, pH7.0), followed by re-equilibrating with buffer solution A and eluting with elution buffer B (0.5M NaCl, 20 mM PB, pH7.0). The eluate was then dialyzed against PBS for buffer exchange. All of the GLP-2 mutant fusion proteins share similar purification procedures, due to similar properties they have, highly specific affinity of Protein A column to Fc fragments (although degradation products cannot be completely removed), and the removal of impurity secreted by host yeast cells with Super Q. FIG. 2 shows the result of some samples of purified GLP-2 mutant fusion proteins. The recombinant protein concentration was determined with BCA.

Example 4: Analysis on Physical and Chemical Properties of Fusion Proteins

Physical and chemical properties of purified proteins were determined by SDS-PAGE, SEC-HPLC, RP-HPLC, mass spectra and the like. As shown in FIG. 1, the recombinant proteins expressed in GS115 have molecular weights consistent with their theoretical molecular weight. GLP-2 mutant fusion proteins with peptide linkers of $(XSSGAPPPS)_u$-$G/S$-$(G-W_1-W_2)$ show a single band in SDS-PAGE (FIG. 1B) and molecular weights between 44 and 29 KD. Degradation and covalent aggregation were not obvious. However, GLP-2 mutant fusion proteins without peptide linkers of (XSSGAPPPS)$_u$-G/S-(G-W$_1$-W$_2$)$_m$ or with other peptide linkers show several bands lower than the theoretical one (FIG. 1A), which were considered as degradation products. The SEC-HPLC analysis of purified samples was performed with Sepax SRT SEC-300 (7.8*300 mm, 5 μm, 300 Å). 100 mM PBS, pH6.4 was used as the mobile phase. The results showed that, compared with GLP-2 mutant fusion proteins (SEQ ID NO:10-11 and SEQ ID NO:23-27) with G/S peptide linkers only and SEQ ID NO:9 without peptide linker, GLP-2 mutant fusion proteins with peptide linkers of G/S-(G-W$_1$-W$_2$)$_m$ (SEQ ID NO:12-22) showed a single peak on an SEC column, no aggregation or degradation peaks observed. A GLP-2 mutant fusion protein (SEQ ID NO:9) without peptide linker showed several peaks of degradation and aggregation. Furthermore, samples of SEQ ID NO:28-29 further containing unit XSSGAPPPS also showed significant decrease in aggregates (Table 3).

TABLE 3

Analysis on aggregates of GLP-2 mutant Fusion Protein in SEC-HPLC

| SEQ ID NO: | MonomerX̌ (%) |
|---|---|
| 9 | 26 |
| 10 | 30 |
| 11 | 21 |
| 12 | 95 |
| 16 | 99 |
| 17 | 99 |
| 18 | 98 |
| 19 | 96 |
| 20 | 94 |
| 21 | 94 |
| 22 | 96 |
| 23 | 27 |
| 24 | 17 |
| 25 | 23 |
| 26 | 29 |
| 27 | 21 |
| 28 | 89 |
| 29 | 91 |

MonomerX̌: refers herein to active molecules formed by two Fc chains through covalent bonds.

Only monomer contents are shown in the table, and the data are the average of purified recombinant proteins of 3 batches of fermentation broths.

Purified samples were analyzed with RP-HPLC using Phenomenex Jupiter C4 (4.6*150 mm, 5 μm, 300 Å) with 0.1% TFA+water (A) and 0.1% TFA+acetonitrile (B) as the mobile phase in a gradient of 5% B-100% B (0-30 min). The result demonstrates that, consistent with the electrophoresis, GLP-2 mutant fusion proteins with peptide linkers of (XSSGAPPPS)$_u$-G/S-(GW$_1$-W$_2$)$_m$ show a single peak in RP column, while the GLP-2 mutant fusion protein with other peptide linkers or without a peptide linker show several peaks of degradation products.

The MS analysis result of purified samples demonstrates that GLP-2 mutant fusion proteins with peptide linker of (XSSGAPPPS)$_u$-G/S-(G-W$_1$-W$_2$)$_m$ show major peaks consistent with their theoretical molecular weights (≥90%), while minor peaks corresponding to N-terminally truncated products cannot be detected by electrophoresis and RP-HPLC (≤10%). Other GLP-2 mutant fusion proteins showed minor peaks consistent with their theoretical molecular weights (≤20%), most peaks showed molecular weights smaller than their theoretical counterparts, indicating degradation did occur.

Example 5: In Vitro Cell-Based Assay

Cell-based assay of the GLP-2 fusion protein were carried out with luciferase reporter gene. To construct recombinant expression plasmid pCDNA3.1-GLP-2R, GLP-2R gene was cloned into mammalian cell expression plasmid pCDNA3.1, and the full-length luciferase gene was cloned into plasmid pCRE-EGFP to replace gene EGFP and obtain recombinant plasmid pCRE-Luc. Plasmids pCDNA3.1-GLP-2R and pCRE-Luc were transfected into CHO cells at a molar ratio of 1:10. A recombinant stable transfected cell line of GLP-2R/Luc-CHO was obtained after screening.

Cells were cultured in DMEM/F12 medium containing 10% FBS and 300 μg/ml G418 in a 10-cm cell culture dish, and the culture supernatant was discarded when cell confluency was about 90%. After digested with 2 ml of trypsin for 2 min, the cell culture was neutralized with 2 ml of DMEM/F12 medium containing 10% FBS and 300 μg/ml G418, then transferred into a 15 ml centrifuge tube, and centrifuged at 800 rpm for 5 min. After centrifugation, supernatant was discarded and 2 ml of DMEM/F12 medium containing 10% FBS and 300 μg/ml G418 was used to resuspend the pellet followed by cell number counting. The cells were diluted with DMEM/F12 medium containing 10% FBS to 3*10$^5$/ml, and 100 μl was seeded in each well of a 96-well plate, i.e., 30,000 cells/well. Cells were cultured in DMEM/F12 medium containing 0.1% FBS after adhesion.

The supernatant in the 96-well plate was discarded after overnight culture. The recombinant protein purified in Example 3 was diluted to a series of specified concentrations with DMEM/F12 medium containing 0.1% FBS, then pipetted 100 μl/well to a cell culture plate. Fluorescence was measured 6 h later. The assay followed the manual of the lucifersae reporter kit (Ray Biotech, Cat: 68-LuciR-S200). The results are shown in Table 3. Discrepancy of the peptide linkers is thought to contribute to the activity difference because of their different effects on steric hindrance and degradation. For samples of SEQ ID NO:9-11 or 23-27, the aggregate formation (Example 4) may further reduces their activities.

TABLE 3

Results of in vitro Cell-Based Activity Assay of GLP-2 mutant Fusion Proteins

| SEQ ID NO: | EC50 (nM) |
|---|---|
| 9 | 85.8 |
| 10 | 80.2 |
| 11 | 92.6 |
| 12 | 25.8 |
| 13 | 19.6 |
| 14 | 21.9 |
| 15 | 24.1 |
| 16 | 7.8 |
| 17 | 6.4 |
| 18 | 10.7 |
| 19 | 11.0 |
| 20 | 13.1 |
| 21 | 14.4 |
| 22 | 12.5 |
| 23 | 82.4 |
| 24 | 95.8 |
| 25 | 83.4 |
| 26 | 81.7 |
| 27 | 92.1 |
| 28 | 23.2 |
| 29 | 27.3 |
| 2 (A2G) | 1.8 |

Example 6: Determination of Pharmacodynamics Profiles in Animal Models

Chemotherapy drugs for cancer care treatment exhibit cytotoxicity by inducing apoptosis and cell cycle arrest.

Intestinal epithelial cells are most readily subjected to cytotoxicity and lead to gastrointestinal mucosa inflammation, diarrhea and bacteremia, which get no reliable preventive treatment so far. GLP-2 has been proven to have significant anti-apoptotic effects on intestinal crypt cells and relieves the intestinal mucositis caused by chemotherapy drugs. In this example, the in vivo physiological activities of the GLP-2 mutant fusion proteins were compared in rat models.

SD rats were divided into 8 groups, each comprising 6 animals (male and female in half): 1) fluorouracil (5-FU)+ GLP-2 mutant 1 (SEQ ID NO:16); 2) fluorouracil (5-FU)+ GLP-2 mutant 2 (SEQ ID NO:17); 3) fluorouracil (5-FU)+ GLP-2 mutant 3 (SEQ ID NO:18); 4) fluorouracil (5-FU)+ GLP-2 mutant 4 (SEQ ID NO:9); 5) fluorouracil (5-FU)+ GLP-2 mutant 5 (SEQ ID NO:10); 6) fluorouracil (5-FU)+ GLP-2 mutant 6 (SEQ ID NO:25); 7) fluorouracil (5-FU)+ normal saline; and 8) saline. Body weight of each rat was recorded. GLP-2 mutants were subcutaneously injected to the rats 3 days before the injection of 5-FU: group 1) to 6) at a dose of 25 nmol/kg once a day for 7 days, while groups 7) and 8) saline of the same volume. On day 4 to 7, 5-FU was intraperitoneally injected to the rats in group 1) to group 7) at a dose of 50 mg/kg, and 24 h after the last injection of 5-FU, all rats were sacrificed. Abdominal cavities of the rats were cut off, small intestines and large intestines were cut out in an ice bath followed by rinsing with saline. Finally their lengths and wet weights were measured. The ratios of the small intestine weight to body weight were calculated. The protective effects of different GLP-2 mutant fusion proteins on the intestinal tract are shown in FIG. 3.

Figure 3:
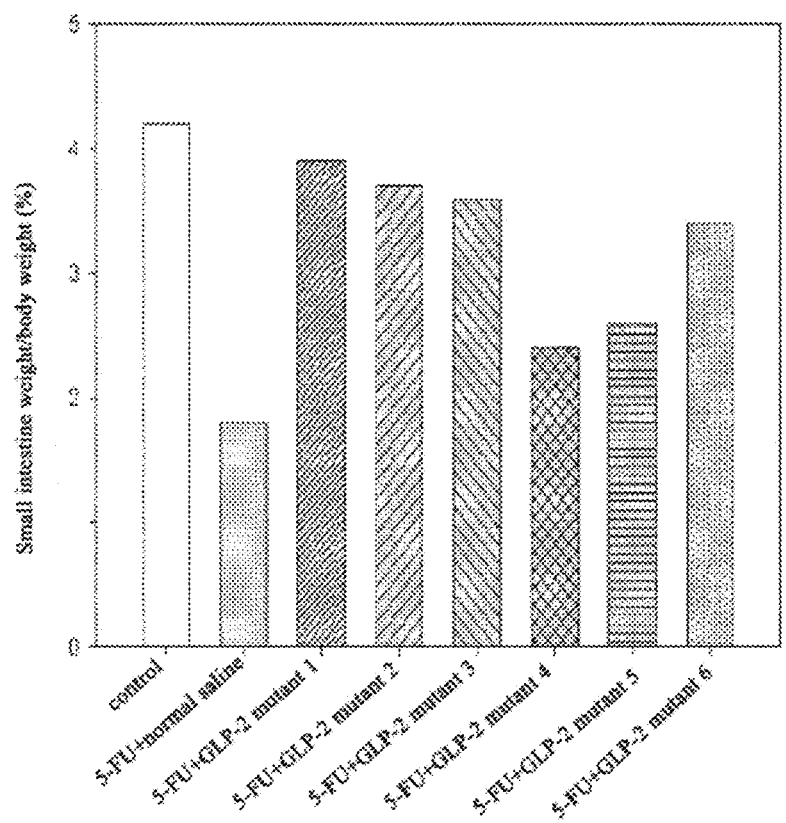
FIG. 3 shows the effect of GLP-2 mutant fusion proteins on the ratio of the small intestine weight to body weight of rats.

As shown in FIG. 3, compared with the 5-FU+saline control group, GLP-2 mutants 1 to 6 significantly relieve 5-FU induced injury to the small intestine, while mutants 1-3 have better curative effects than mutants 4-6, indicating consistency between in vivo pharmacodynamics profiles and the cell-based activities in vitro. The standard deviations (SD) of the pharmacodynamic data from the 6 animals in each group were calculated as follows: control group, 5-FU+saline group, 5-FU+mutant 1 group, 5-FU+mutant 2 group, 5-FU+mutant 3 group, 5-FU+mutant 4 group, 5-FU+mutant 5 group and 5-FU+mutant 6 group are 4.21±0.79, 1.88±0.24, 3.85±0.53, 3.77±0.22, 3.58±0.73, 2.48±0.44, 2.76±0.27 and 3.41±0.14, respectively.

The foregoing embodiments are only to illustrate the principle and efficacy of the present disclosure exemplarily, and are not to limit the present disclosure.

What is claimed is:

1. A fusion protein, wherein the structure characterized as follows:

R-L-P, wherein

R is a GLP-2 receptor agonist;

P is a long-acting carrier protein;

L is a peptide linker and is represented by the following formula:

(XSSGAPPPS)-G/S-(G-$W_1$-$W_2$)$_m$, wherein

X is selected from a group consisting of P, GP, GGP and NGGP;

G/S is a peptide consisting of G and S in arbitrary combination and with 5 to 25 amino acids in length;

$W_1$ and $W_2$ are selected from a group consisting of 19 natural amino acid residues except Cys, respectively;

u is 0 or 1; and m is an integer of 1 to 20; and

L is selected from SEQ ID NO: 30, SEQ ID NO: 31 and SEQ ID NO. 32, wherein, the fusion protein is selected from SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26, SEQ ID NO: 27, SEQ ID NO: 28, and SEQ ID NO: 29.

2. A nucleotide sequence, encoding the fusion protein according to claim 1.

3. A recombinant expression vector, carrying the nucleotide sequence according to claim 2.

4. A host cell, transforming the recombinant expression vector according to claim 3.

5. A pharmaceutical composition, comprising the fusion protein according to claim 1, and a pharmaceutically acceptable diluter, carrier or excipient, wherein the fusion protein is selected from SEQ ID NO: 9, SEQ ID NO: 10, SEQ ID NO: 16, SEQ ID NO: 17, SEQ ID NO: 18 and SEQ ID NO: 25.

6. The fusion protein according to claim 1, wherein the fusion protein is selected from SEQ ID NO: 16, SEQ ID NO: 17 and SEQ ID NO: 18.

7. A method of treating gastrointestinal injury, short bowel syndrome and Crohn's enteritis caused by chemotherapy by administering a therapeutically effective amount of a pharmaceutical composition according to claim 5 to a subject in need.

* * * * *